(12) United States Patent
Cabrera et al.

(10) Patent No.: US 11,399,836 B2
(45) Date of Patent: Aug. 2, 2022

(54) ADAPTER, EXTENSION, AND CONNECTOR ASSEMBLIES FOR SURGICAL DEVICES

(71) Applicant: Covidien LP, Mansfield, MA (US)

(72) Inventors: Ramiro Cabrera, Cheshire, CT (US); Anne Nelson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 232 days.

(21) Appl. No.: 16/262,242

(22) Filed: Jan. 30, 2019

(65) Prior Publication Data

US 2019/0159781 A1    May 30, 2019

Related U.S. Application Data

(62) Division of application No. 14/875,766, filed on Oct. 6, 2015, now Pat. No. 10,226,254.

(60) Provisional application No. 62/066,518, filed on Oct. 21, 2014.

(51) Int. Cl.
*A61B 17/115* (2006.01)
*A61B 17/00* (2006.01)

(52) U.S. Cl.
CPC ... *A61B 17/1155* (2013.01); *A61B 2017/0046* (2013.01); *A61B 2017/00367* (2013.01); *A61B 2017/00398* (2013.01); *A61B 2017/00473* (2013.01); *A61B 2017/00477* (2013.01)

(58) Field of Classification Search
CPC ...... A61B 17/1155; A61B 2017/00367; A61B 2017/00398; A61B 2017/0046; A61B 2017/00473; A61B 2017/00477
USPC .......................................... 227/175.1–182.1
See application file for complete search history.

(56) References Cited

U.S. PATENT DOCUMENTS

| | | | |
|---|---|---|---|
| 2,777,340 A | 1/1957 | Hettwer et al. | |
| 2,957,353 A | 10/1960 | Babacz | |
| 3,111,328 A | 11/1963 | Di Rito et al. | |
| 3,651,720 A * | 3/1972 | Indyk | B25B 13/06 |
| | | | 81/124.5 |
| 3,695,058 A | 10/1972 | Keith, Jr. | |

(Continued)

FOREIGN PATENT DOCUMENTS

| | | |
|---|---|---|
| CA | 2451558 A1 | 1/2003 |
| CA | 2824590 A1 | 4/2014 |

(Continued)

OTHER PUBLICATIONS

Japanese Office Action dated May 28, 2019, issued in JP Appln. No. 2015-206306.

(Continued)

*Primary Examiner* — Robert F Long
(74) *Attorney, Agent, or Firm* — Carter, DeLuca & Farrell LLP

(57) ABSTRACT

An assembly including an adapter assembly and an extension assembly for connecting an end effector to an electrosurgical instrument is provided. The adapter assembly includes first and second pusher assemblies configured for converting rotational motion into linear motion and a drive member for transferring rotational motion. The extension assembly includes at least one flexible band assembly for transferring the linear motion from the adapter assembly and a trocar assembly configured for converting rotational motion into linear motion. Also provided is a connection assembly for connecting a first tubular member to a second tubular member.

18 Claims, 29 Drawing Sheets

(56) References Cited

U.S. PATENT DOCUMENTS

| | | | | |
|---|---|---|---|---|
| 3,734,515 | A | 5/1973 | Dudek | |
| 3,759,336 | A | 9/1973 | Marcovitz et al. | |
| 4,162,399 | A | 7/1979 | Hudson | |
| 4,473,077 | A * | 9/1984 | Noiles | A61B 17/115 227/179.1 |
| 4,606,343 | A | 8/1986 | Conta et al. | |
| 4,705,038 | A | 11/1987 | Sjostrom et al. | |
| 4,722,685 | A | 2/1988 | de Estrada et al. | |
| 4,823,807 | A | 4/1989 | Russell et al. | |
| 4,874,181 | A | 10/1989 | Hsu | |
| 5,129,118 | A | 7/1992 | Walmesley | |
| 5,129,570 | A | 7/1992 | Schulze et al. | |
| 5,152,744 | A | 10/1992 | Krause et al. | |
| 5,205,459 | A * | 4/1993 | Brinkerhoff | A61B 17/115 227/179.1 |
| 5,301,061 | A | 4/1994 | Nakada et al. | |
| 5,312,023 | A | 5/1994 | Green et al. | |
| 5,326,013 | A | 7/1994 | Green et al. | |
| 5,350,104 | A * | 9/1994 | Main | A61B 17/115 227/179.1 |
| 5,350,355 | A | 9/1994 | Sklar | |
| 5,383,874 | A | 1/1995 | Jackson et al. | |
| 5,383,880 | A | 1/1995 | Hooven | |
| 5,389,098 | A | 2/1995 | Tsuruta et al. | |
| 5,391,156 | A * | 2/1995 | Hildwein | A61B 17/29 604/174 |
| 5,395,033 | A | 3/1995 | Byrne et al. | |
| 5,400,267 | A | 3/1995 | Denen et al. | |
| 5,411,508 | A | 5/1995 | Bessler et al. | |
| 5,413,267 | A | 5/1995 | Solyntjes et al. | |
| 5,427,087 | A | 6/1995 | Ito et al. | |
| 5,433,721 | A | 7/1995 | Hooven et al. | |
| 5,467,911 | A | 11/1995 | Tsuruta et al. | |
| 5,476,379 | A | 12/1995 | Disel | |
| 5,487,499 | A | 1/1996 | Sorrentino et al. | |
| 5,518,163 | A | 5/1996 | Hooven | |
| 5,518,164 | A | 5/1996 | Hooven | |
| 5,526,822 | A | 6/1996 | Burbank et al. | |
| 5,529,235 | A | 6/1996 | Boiarski et al. | |
| 5,535,934 | A | 7/1996 | Boiarski et al. | |
| 5,535,937 | A | 7/1996 | Boiarski et al. | |
| 5,540,375 | A | 7/1996 | Bolanos et al. | |
| 5,540,706 | A | 7/1996 | Aust et al. | |
| 5,542,594 | A | 8/1996 | McKean et al. | |
| 5,549,637 | A * | 8/1996 | Crainich | A61B 17/29 606/170 |
| 5,553,675 | A | 9/1996 | Pitzen et al. | |
| 5,562,239 | A | 10/1996 | Boiarski et al. | |
| 5,564,615 | A | 10/1996 | Bishop et al. | |
| 5,609,560 | A | 3/1997 | Ichikawa et al. | |
| 5,626,587 | A | 5/1997 | Bishop et al. | |
| 5,632,432 | A | 5/1997 | Schulze et al. | |
| 5,645,209 | A | 7/1997 | Green et al. | |
| 5,647,526 | A | 7/1997 | Green et al. | |
| 5,653,374 | A | 8/1997 | Young et al. | |
| 5,658,300 | A | 8/1997 | Bito et al. | |
| 5,662,662 | A | 9/1997 | Bishop et al. | |
| 5,667,517 | A | 9/1997 | Hooven | |
| 5,693,042 | A | 12/1997 | Boiarski et al. | |
| 5,704,534 | A | 1/1998 | Huitema et al. | |
| 5,713,505 | A | 2/1998 | Huitema | |
| 5,762,603 | A | 6/1998 | Thompson | |
| 5,779,130 | A | 7/1998 | Alesi et al. | |
| 5,782,396 | A | 7/1998 | Mastri et al. | |
| 5,782,397 | A | 7/1998 | Koukline | |
| 5,792,573 | A | 8/1998 | Pitzen et al. | |
| 5,797,536 | A | 8/1998 | Smith et al. | |
| 5,820,009 | A | 10/1998 | Melling et al. | |
| 5,863,159 | A | 1/1999 | Lasko | |
| 5,908,427 | A | 6/1999 | McKean et al. | |
| 5,954,259 | A | 9/1999 | Viola et al. | |
| 5,964,774 | A | 10/1999 | McKean et al. | |
| 5,993,454 | A | 11/1999 | Longo | |
| 6,010,054 | A | 1/2000 | Johnson et al. | |
| 6,017,354 | A | 1/2000 | Culp et al. | |
| 6,032,849 | A | 3/2000 | Mastri et al. | |
| 6,045,560 | A | 4/2000 | McKean et al. | |
| 6,090,123 | A | 7/2000 | Culp et al. | |
| 6,126,651 | A | 10/2000 | Mayer | |
| 6,129,547 | A | 10/2000 | Cise et al. | |
| 6,165,169 | A | 12/2000 | Panescu et al. | |
| 6,239,732 | B1 | 5/2001 | Cusey | |
| 6,241,139 | B1 | 6/2001 | Milliman et al. | |
| 6,264,086 | B1 | 7/2001 | McGuckin, Jr. | |
| 6,264,087 | B1 | 7/2001 | Whitman | |
| 6,302,311 | B1 | 10/2001 | Adams et al. | |
| 6,315,184 | B1 | 11/2001 | Whitman | |
| 6,321,855 | B1 | 11/2001 | Barnes | |
| 6,329,778 | B1 | 12/2001 | Culp et al. | |
| 6,343,731 | B1 | 2/2002 | Adams et al. | |
| 6,348,061 | B1 | 2/2002 | Whitman | |
| 6,368,324 | B1 | 4/2002 | Dinger et al. | |
| 6,371,909 | B1 | 4/2002 | Hoeg et al. | |
| 6,434,507 | B1 | 8/2002 | Clayton et al. | |
| 6,443,973 | B1 | 9/2002 | Whitman | |
| 6,461,372 | B1 | 10/2002 | Jensen et al. | |
| 6,488,197 | B1 | 12/2002 | Whitman | |
| 6,491,201 | B1 | 12/2002 | Whitman | |
| 6,533,157 | B1 | 3/2003 | Whitman | |
| 6,537,280 | B2 | 3/2003 | Dinger et al. | |
| 6,610,066 | B2 | 8/2003 | Dinger et al. | |
| 6,611,793 | B1 | 8/2003 | Burnside et al. | |
| 6,645,218 | B1 | 11/2003 | Cassidy et al. | |
| 6,654,999 | B2 | 12/2003 | Stoddard et al. | |
| 6,681,979 | B2 | 1/2004 | Whitman | |
| 6,695,199 | B2 | 2/2004 | Whitman | |
| 6,698,643 | B2 | 3/2004 | Whitman | |
| 6,699,177 | B1 | 3/2004 | Wang et al. | |
| 6,716,233 | B1 | 4/2004 | Whitman | |
| 6,743,240 | B2 | 6/2004 | Smith et al. | |
| 6,783,533 | B2 | 8/2004 | Green et al. | |
| 6,792,390 | B1 | 9/2004 | Burnside et al. | |
| 6,793,652 | B1 | 9/2004 | Whitman et al. | |
| 6,817,508 | B1 | 11/2004 | Racenet et al. | |
| 6,830,174 | B2 | 12/2004 | Hillstead et al. | |
| 6,835,199 | B2 * | 12/2004 | McGuckin, Jr | A61B 17/105 606/142 |
| 6,846,308 | B2 | 1/2005 | Whitman et al. | |
| 6,846,309 | B2 | 1/2005 | Whitman et al. | |
| 6,849,071 | B2 | 2/2005 | Whitman et al. | |
| 6,860,892 | B1 | 3/2005 | Tanaka et al. | |
| 6,899,538 | B2 | 5/2005 | Matoba | |
| 6,905,057 | B2 | 6/2005 | Swayze et al. | |
| 6,959,852 | B2 | 11/2005 | Shelton, IV et al. | |
| 6,964,363 | B2 | 11/2005 | Wales et al. | |
| 6,981,628 | B2 | 1/2006 | Wales | |
| 6,981,941 | B2 | 1/2006 | Whitman et al. | |
| 6,986,451 | B1 | 1/2006 | Mastri et al. | |
| 6,988,649 | B2 | 1/2006 | Shelton, IV et al. | |
| 7,032,798 | B2 | 4/2006 | Whitman et al. | |
| RE39,152 | E | 6/2006 | Aust et al. | |
| 7,055,731 | B2 | 6/2006 | Shelton, IV et al. | |
| 7,059,508 | B2 | 6/2006 | Shelton, IV et al. | |
| 7,077,856 | B2 | 7/2006 | Whitman | |
| 7,111,769 | B2 | 9/2006 | Wales et al. | |
| 7,122,029 | B2 | 10/2006 | Koop et al. | |
| 7,140,528 | B2 | 11/2006 | Shelton, IV | |
| 7,141,049 | B2 | 11/2006 | Stern et al. | |
| 7,143,923 | B2 | 12/2006 | Shelton, IV et al. | |
| 7,143,925 | B2 | 12/2006 | Shelton, IV et al. | |
| 7,143,926 | B2 | 12/2006 | Shelton, IV et al. | |
| 7,147,138 | B2 | 12/2006 | Shelton, IV | |
| 7,172,104 | B2 | 2/2007 | Scirica et al. | |
| 7,225,964 | B2 | 6/2007 | Mastri et al. | |
| 7,238,021 | B1 | 7/2007 | Johnson | |
| 7,246,734 | B2 | 7/2007 | Shelton, IV | |
| 7,252,660 | B2 | 8/2007 | Kunz | |
| 7,328,828 | B2 | 2/2008 | Ortiz et al. | |
| 7,364,060 | B2 * | 4/2008 | Milliman | A61B 17/068 227/175.1 |
| 7,364,061 | B2 | 4/2008 | Swayze et al. | |
| 7,380,695 | B2 | 6/2008 | Doll et al. | |
| 7,380,696 | B2 | 6/2008 | Shelton, IV et al. | |

(56) References Cited

U.S. PATENT DOCUMENTS

| | | |
|---|---|---|
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 * | 4/2011 | Zemlok ............... G16Z 99/00 227/176.1 |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,246,637 B2 * | 8/2012 | Viola ................. A61B 17/0625 606/144 |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,460,275 B2 * | 6/2013 | Taylor ................ A61B 17/0469 606/1 |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,590,763 B2 | 11/2013 | Milliman |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 * | 3/2015 | Spivey ............... A61B 1/00042 600/102 |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,282,961 B2 | 3/2016 | Whitman et al. |
| 9,282,963 B2 | 3/2016 | Bryant |

(56) References Cited

U.S. PATENT DOCUMENTS

| | | |
|---|---|---|
| 9,295,522 B2 | 3/2016 | Kostrzewski |
| 9,307,986 B2 | 4/2016 | Hall et al. |
| 10,226,254 B2 | 3/2019 | Cabrera et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2005/0165328 A1 | 7/2005 | Heske |
| 2006/0074407 A1* | 4/2006 | Padget ............... A61B 17/3201 606/1 |
| 2006/0085033 A1* | 4/2006 | Criscuolo .......... A61B 17/1155 606/219 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0241692 A1 | 10/2006 | McGuckin et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0114261 A1* | 5/2007 | Ortiz ................... A61B 17/064 227/175.1 |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0036206 A1 | 2/2008 | Li-guo |
| 2008/0058801 A1 | 3/2008 | Taylor et al. |
| 2008/0105730 A1* | 5/2008 | Racenet .............. A61B 17/068 227/176.1 |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0108048 A1* | 4/2009 | Zemlok ............ A61B 17/07207 227/175.1 |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0250501 A1* | 10/2009 | Sonnenschein ...... A61B 17/072 227/176.1 |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0076459 A1* | 3/2010 | Farascioni ........ A61B 17/07207 606/143 |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1* | 12/2010 | Viola ............... A61B 17/07207 227/176.1 |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0181029 A1* | 7/2013 | Milliman ............ A61B 17/068 227/175.1 |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005677 A1* | 1/2014 | Shelton, IV ........... B23K 26/40 606/130 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0114334 A1* | 4/2014 | Olson .................... A61B 34/37 606/169 |
| 2014/0138423 A1* | 5/2014 | Whitfield .......... A61B 17/07292 227/176.1 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0257033 A1* | 9/2014 | Frering .................. A61F 5/003 600/37 |

(56) References Cited

U.S. PATENT DOCUMENTS

| | | |
|---|---|---|
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0305992 A1* | 10/2014 | Kimsey ............ A61B 17/07207 227/176.1 |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0108201 A1 | 4/2015 | Williams |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0190133 A1 | 7/2015 | Penna et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0296234 A1* | 10/2016 | Richard ............ A61B 17/1155 |
| 2016/0361057 A1* | 12/2016 | Williams ............ A61B 17/105 |
| 2016/0374667 A1* | 12/2016 | Miller ............ A61B 17/068 227/175.2 |
| 2017/0086879 A1* | 3/2017 | Williams ............ A61B 17/1155 |
| 2017/0196566 A1* | 7/2017 | Sgroi ............ A61B 17/1155 |
| 2019/0090873 A1* | 3/2019 | Fox ............ A61B 17/1155 |
| 2020/0222050 A1* | 7/2020 | Eisinger ............ A61B 17/1155 |
| 2020/0405304 A1* | 12/2020 | Mozdzierz ............ A61B 17/072 |
| 2021/0000472 A1* | 1/2021 | Sgroi, Jr ............ A61B 17/1155 |

FOREIGN PATENT DOCUMENTS

| | | |
|---|---|---|
| CN | 102247182 A | 11/2011 |
| CN | 102551840 A | 7/2012 |
| CN | 103717147 A | 4/2014 |
| DE | 102008053842 A1 | 5/2010 |
| EP | 0705571 A1 | 4/1996 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2668910 A2 | 12/2013 |
| EP | 2684530 A1 | 1/2014 |
| EP | 2883504 A2 | 6/2015 |
| ES | 2333509 A1 | 2/2010 |
| JP | H067357 A | 1/1994 |
| JP | 08038488 | 2/1996 |
| JP | H08182684 A | 7/1996 |
| JP | 2005125075 A | 5/2005 |
| JP | 2011115594 A | 6/2011 |
| JP | 2013248395 A | 12/2013 |
| KR | 20120022521 A | 3/2012 |
| WO | 2006026520 A2 | 3/2006 |
| WO | 2008045333 A2 | 4/2008 |
| WO | 2011108840 A2 | 9/2011 |
| WO | 2012/040984 A1 | 4/2012 |
| WO | 2012/166499 A1 | 12/2012 |
| WO | 2015041845 A2 | 3/2015 |

OTHER PUBLICATIONS

European Search Report dated Dec. 6, 2019, issued in EP Appln. No. 19192171.
European Search Report dated Dec. 13, 2019, issued in EP Appln. No. 19191409.
Partial European Search Report issued in corresponding European Application No. 15190643 dated Feb. 26, 2016.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action dated Dec. 12, 2018, issued in CN Appln. No. 201510843610.
Chinese Office Action dated Sep. 4, 2019, issued in CN Appln. No. 201510843610.
Australian Office Action dated Jul. 23, 2019, issued in AU Appln. No. 2015243004.

(56) References Cited

OTHER PUBLICATIONS

Japanese Office Action (English translation), dated Oct. 23, 2020, corresponding to counterpart Japanese Application No. 2019-175306; 10 pages.

English translation of Japanese Office Action dated Jun. 24, 2021, corresponding to counterpart Japanese Application No. 2019-175306; 8 pages.

* cited by examiner

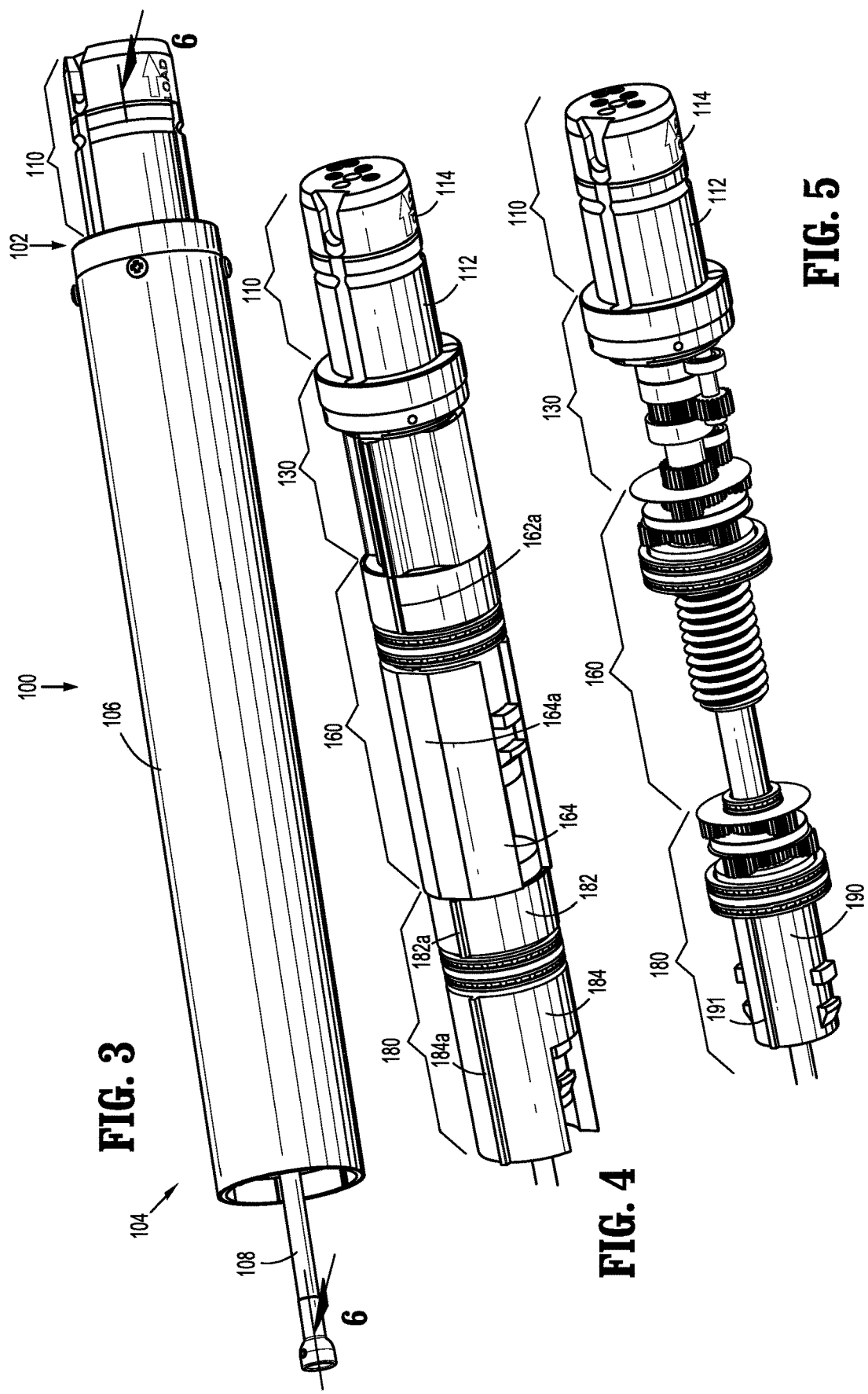

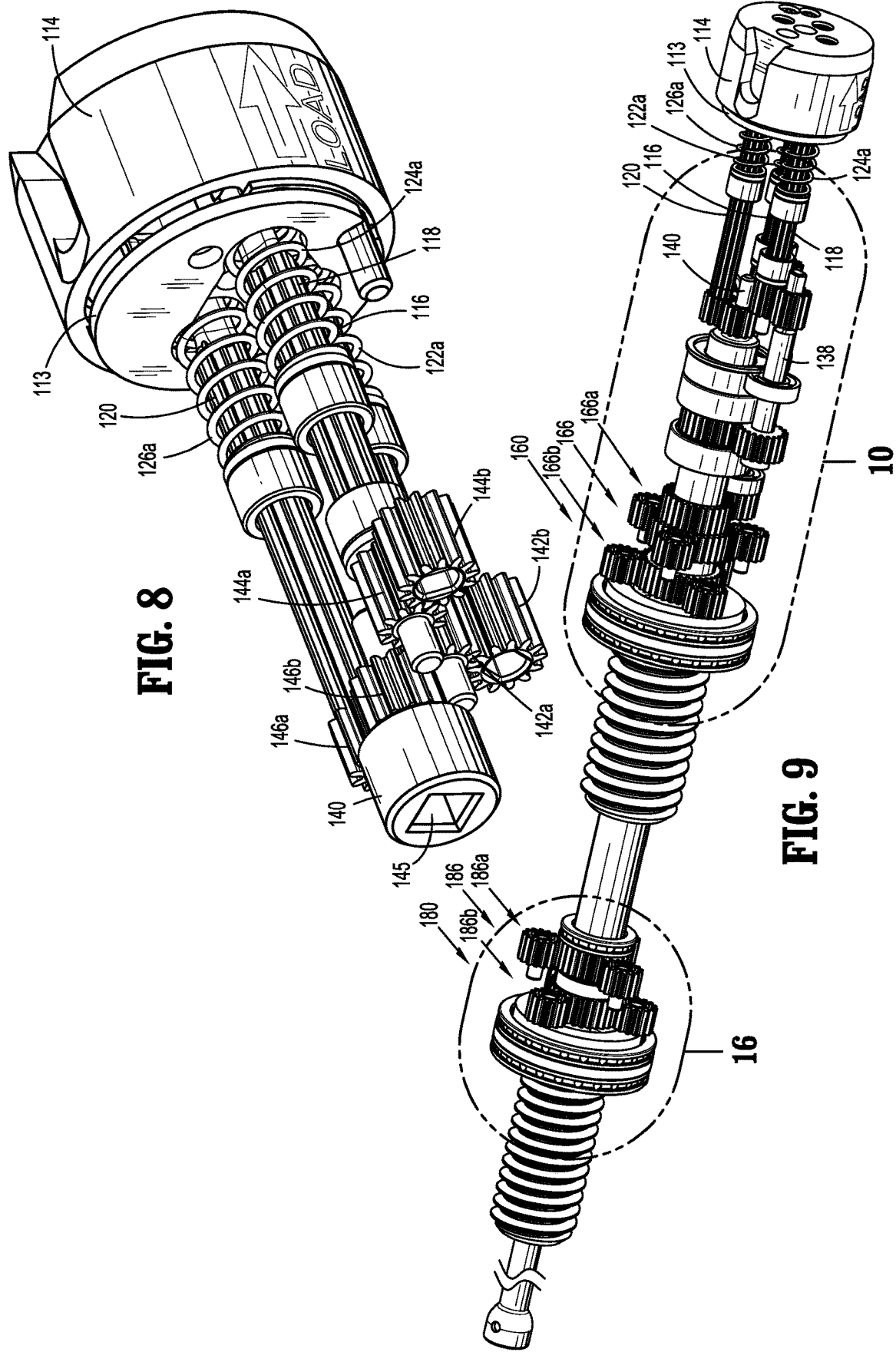

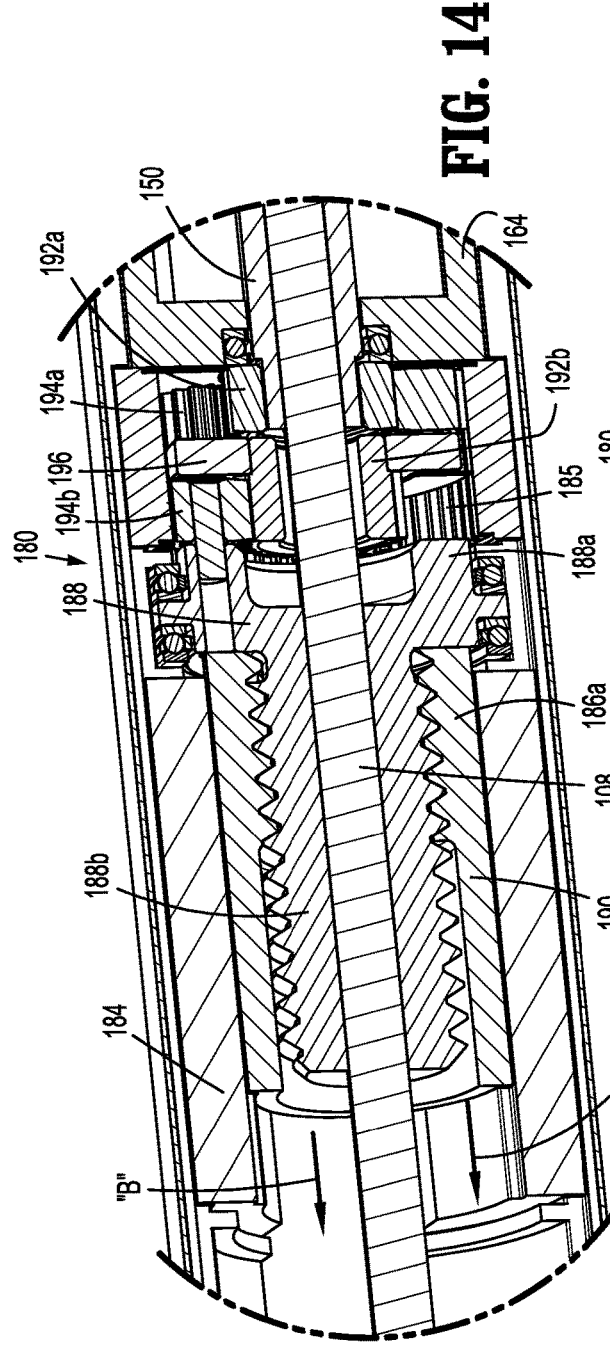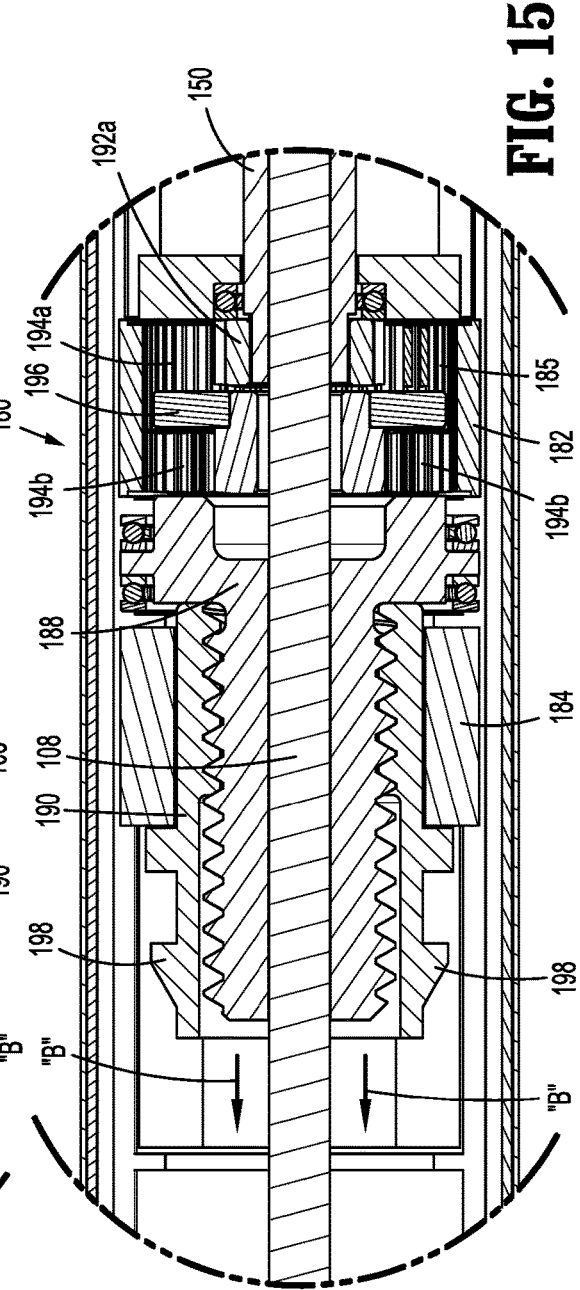

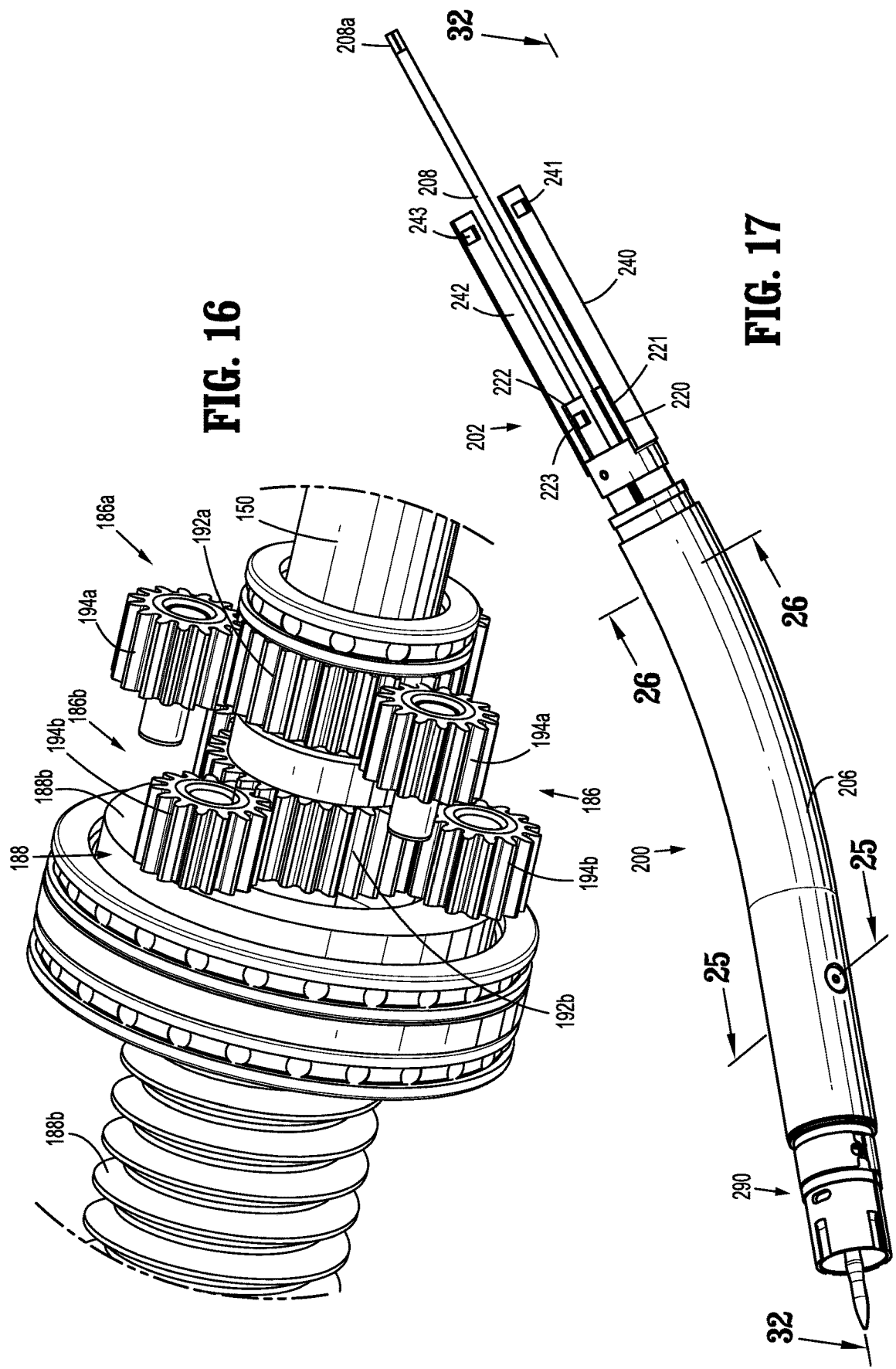

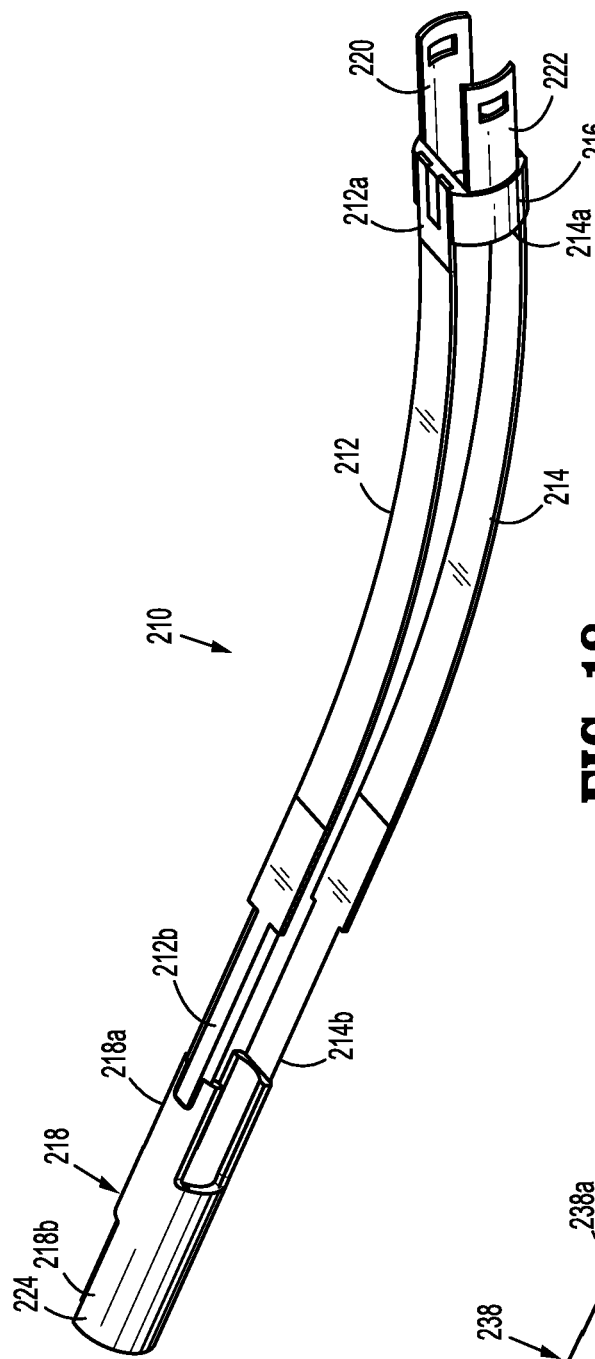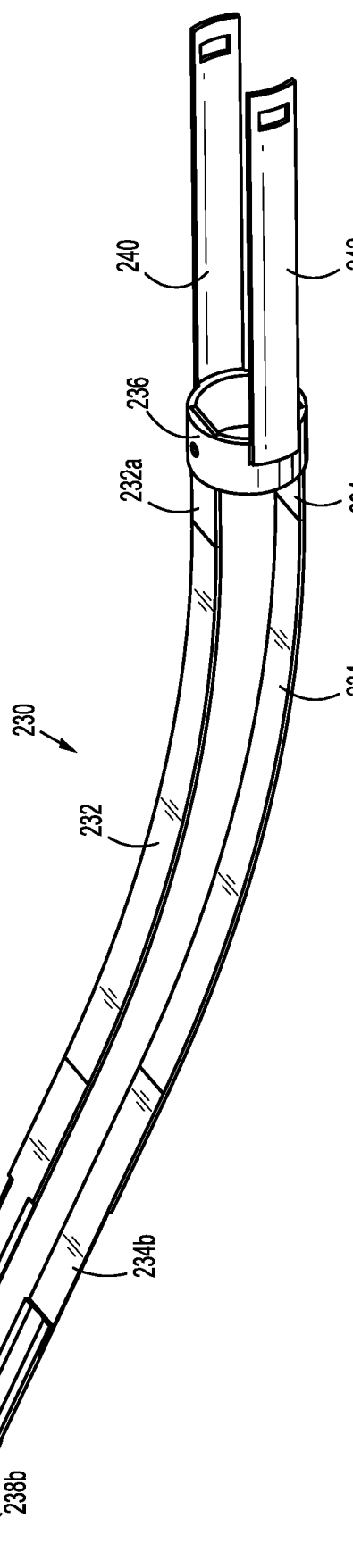

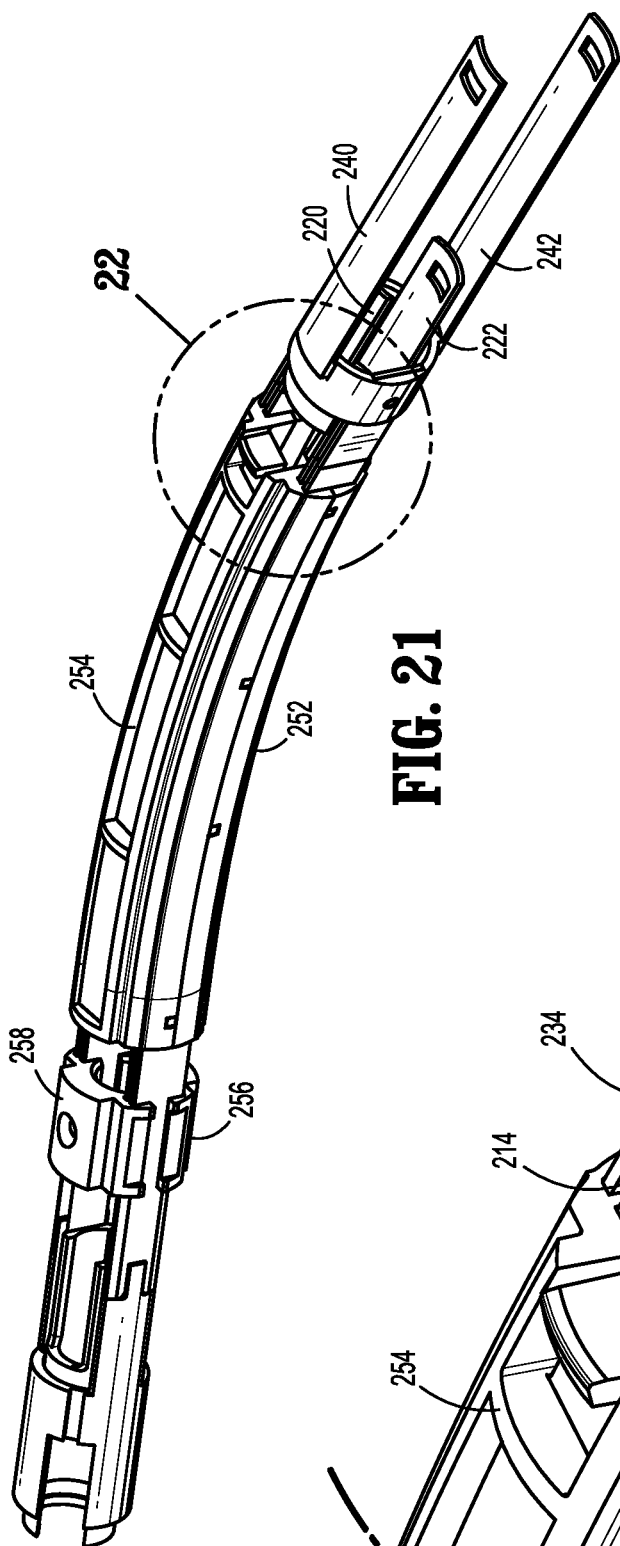
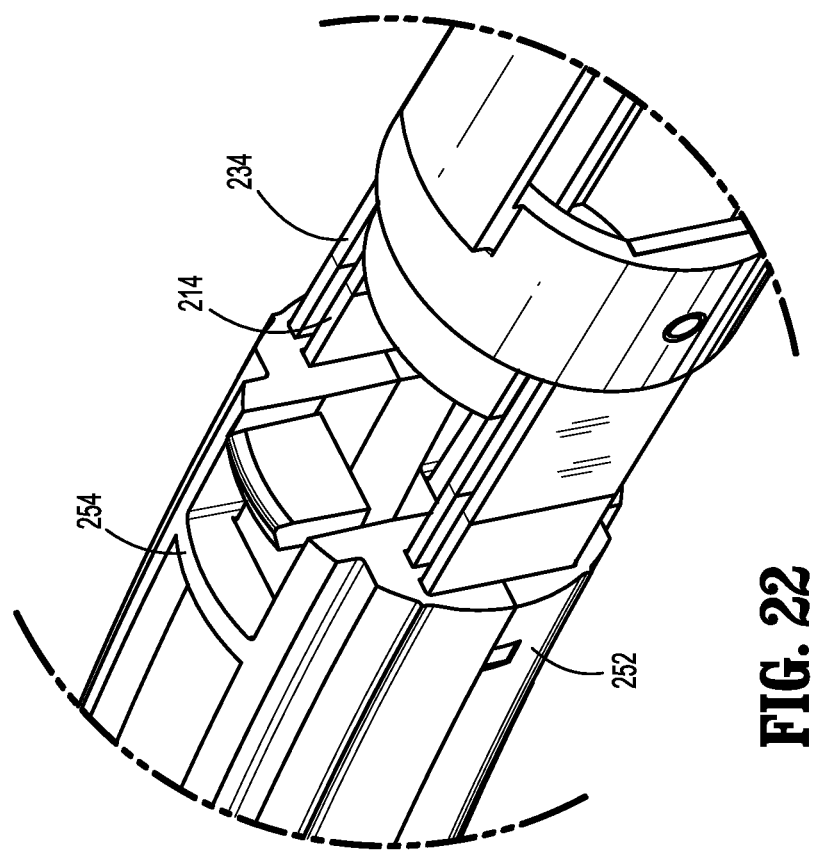
FIG. 21
FIG. 22

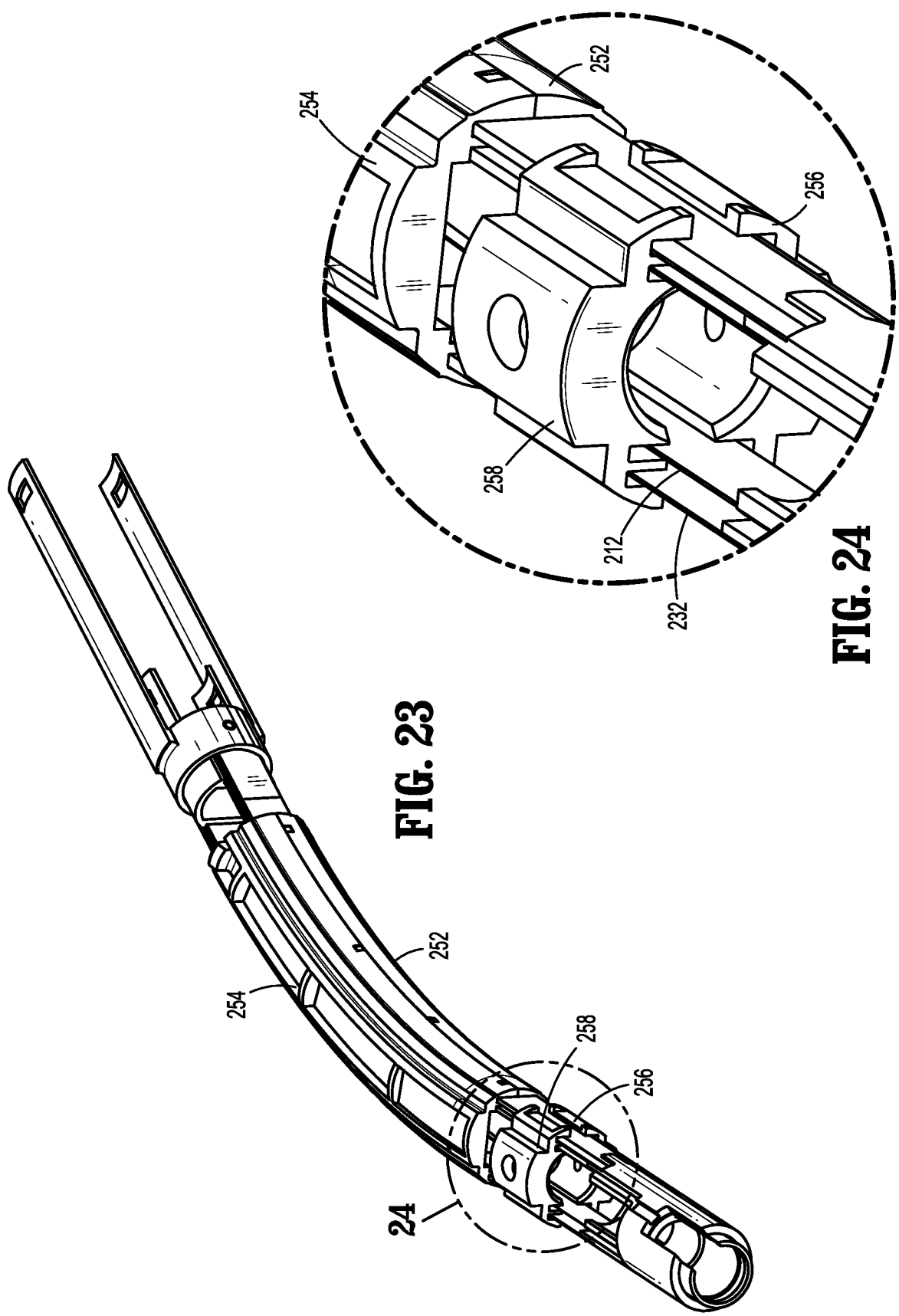

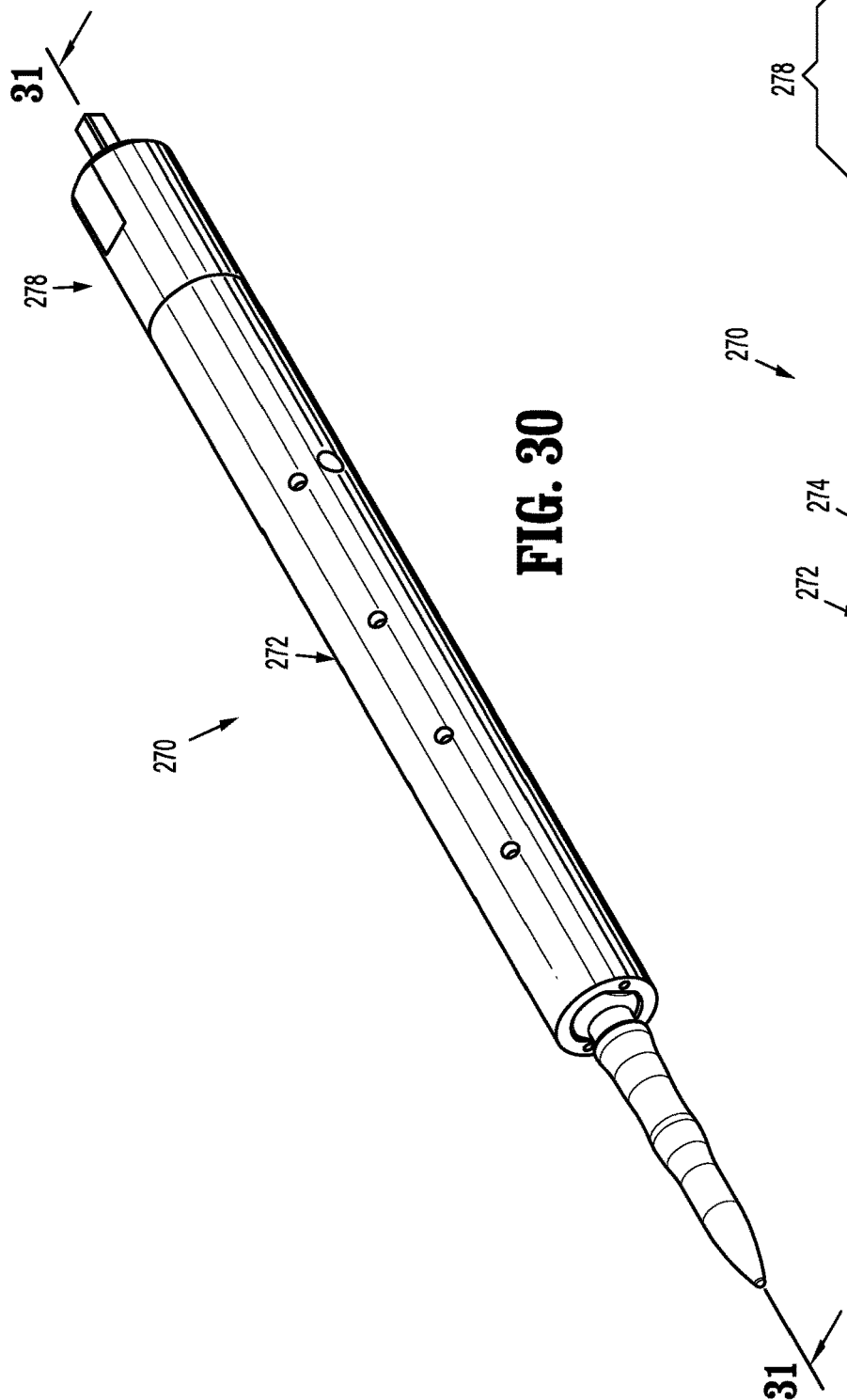
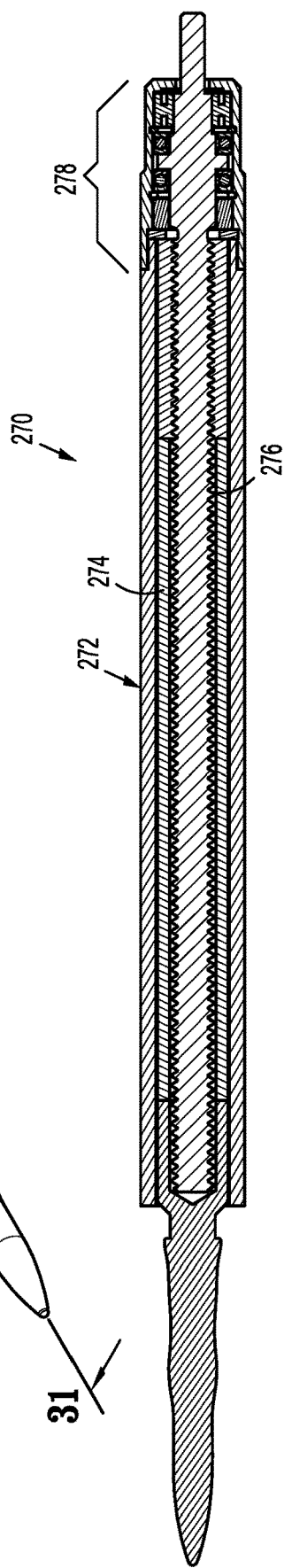
FIG. 30
FIG. 31

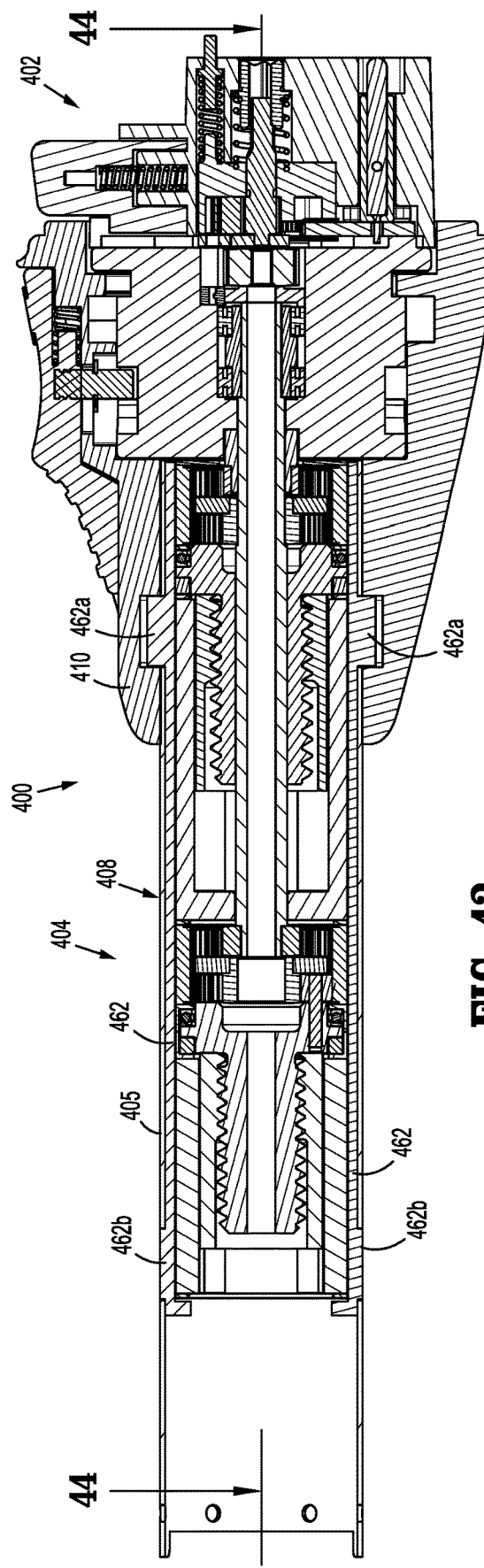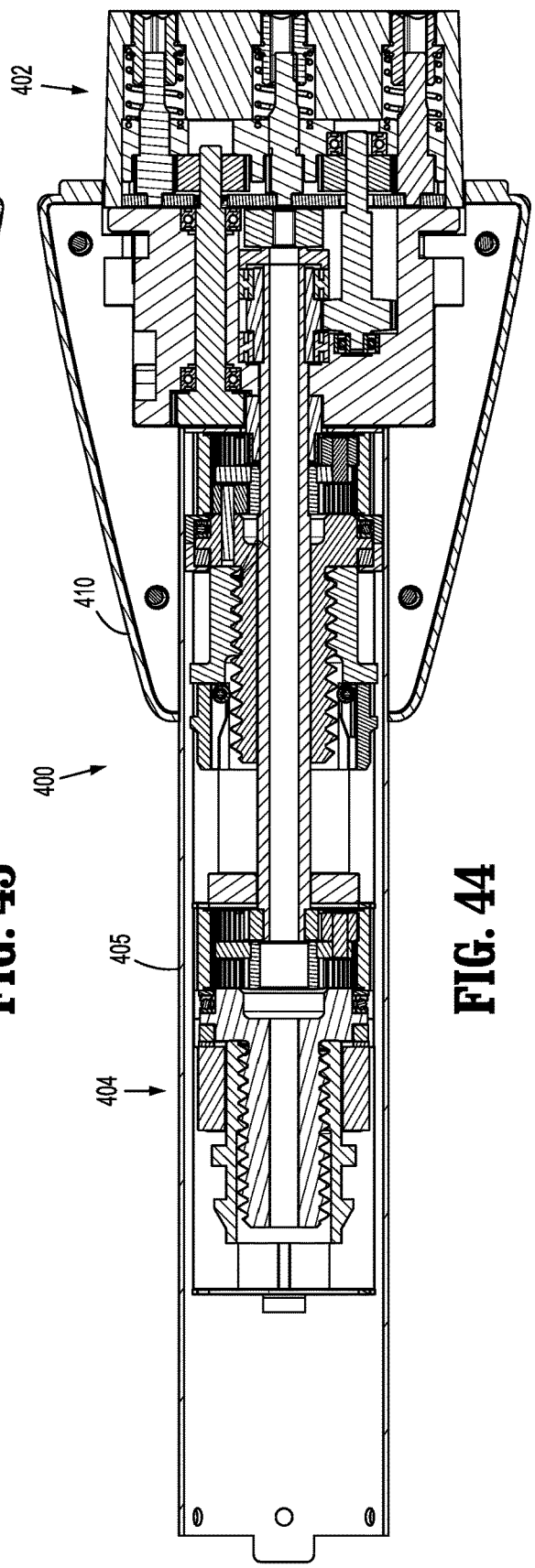
FIG. 43
FIG. 44

ADAPTER, EXTENSION, AND CONNECTOR ASSEMBLIES FOR SURGICAL DEVICES

CROSS-REFERENCE TO RELATED APPLICATIONS

This application is a divisional of U.S. application Ser. No. 14/875,766 filed Oct. 6, 2015, which claims the benefit of and priority to U.S. Provisional Patent Application No. 62/066,518 filed Oct. 21, 2014, the entire disclosures each of which are incorporated by reference herein.

BACKGROUND

1. Technical Field

The present disclosure relates generally to powered surgical devices. More specifically, the present disclosure relates to adapter and extension assemblies for selectively connecting end effectors to the actuation units of the powered surgical devices.

2. Background of Related Art

Powered devices for use in surgical procedures are known. To permit reuse of the handle assemblies of these powered surgical devices and so that the handle assembly may be used with a variety of end effectors, adapter assemblies and extension assemblies have been developed for selective attachment to the handle assemblies and to a variety of end effectors. Following use, the adapter and/or extension assemblies may be disposed of along with the end effector. In some instances, the adapter assemblies and extension assemblies may be sterilized for reuse.

SUMMARY

An assembly for operably connecting an end effector to an electrosurgical instrument is provided. The assembly includes an adapter assembly and an extension assembly. The adapter assembly includes a connector assembly, a drive transfer assembly operably received through the connector assembly and including first, second, and third rotatable shafts, a first pusher assembly operably connected to the first rotatable shaft for converting rotational motion from the first rotatable shaft to longitudinal movement to perform a first function, a second pusher assembly operably connected to the second rotatable shaft for converting rotational motion from the second rotatable shaft to longitudinal movement to perform a second function, and a drive member operably connected to the third rotatable shaft for transferring rotational motion from the third rotatable shaft to perform a third function. The drive transfer assembly and the first and second pusher assemblies are operably received within a single outer tube. The extension is operably connected to a distal end of the adapter assembly and includes at least one flexible band assembly operably connected to one of the first and second pusher assemblies.

In embodiments, the first pusher assembly includes a first planetary gear assembly and the second pusher assembly includes a second planetary gear assembly. Each of the first and second planetary gear assemblies may include a first planetary gear system and a second planetary gear system. Each of the first and second planetary gear systems may be configured to reduce a speed of rotation of the first and second rotatable shafts. The first pusher assembly may include a first drive screw operably connected to the first planetary gear assembly and the second pusher assembly may include a second drive screw operably connected to the second planetary gear assembly. The first pusher assembly may include a first pusher member operably received about the first drive screw and the second pusher assembly may include a second pusher member operably received about the second screw member. Rotation of the first drive screw may cause longitudinal movement of the first pusher member and rotation of the second drive screw may cause longitudinal movement of the second pusher member. The adapter assembly may further include a base and a support structure rotatable relative to the base along a longitudinal axis, the connector assembly and the drive transfer assembly being disposed with in the base and the first and second pusher assemblies being disposed within the support structure. The connection assembly may be configured for operable connection to an electrosurgical instrument.

In some embodiments, the extension assembly includes a second flexible band assembly operably connected to the other of the first and second pusher assemblies. The extension assembly may include a trocar assembly operably connected to the drive member. The trocar assembly may convert rotational motion from the drive member into linear motion. The extension assembly may include a link assembly operably connecting the trocar assembly to the drive member. The link assembly may include a first drive shaft pivotally connected to a second drive shaft and a coupling member pivotally connected to the second drive shaft.

An extension assembly for operably connecting an end effector to an electrosurgical instrument is also provided. The extension assembly includes an outer sleeve, a frame assembly received within the outer sleeve, an inner flexible band assembly slidably disposed within the frame assembly for performing a first function, an outer flexible band assembly slidably disposed within the frame assembly and relative to the inner flexible band assembly for performing a second function, and a trocar assembly disposed within the frame assembly and including a trocar member for performing a third function. The inner flexible band assembly may include a proximal end configured for connection to a first linear drive member and the outer flexible band assembly may include a proximal end configured for connection to a second linear drive member. A proximal end of the trocar assembly may be configured for connection to a rotatable drive shaft. Rotation of the rotatable drive shaft may cause linear advancement of the trocar member. The extension assembly may further include a connection assembly configured for operable connection with an end effector. A distal end of the inner flexible band assembly may include a flange configured for operable connection with an end effector and a distal end of the outer flexible band assembly includes a flange configured for operable connection with an end effector. The trocar member may be configured for operably connection with an anvil assembly. The extension assembly may further include a link assembly for operable connection with the trocar assembly, the link assembly including a first shaft pivotally secured to a second shaft and a coupling member.

Also provided is a connection assembly for securing a first tubular member to a second tubular member. The connection assembly includes a tubular base having a flange and an annular rim. The connection assembly further includes a tubular extension having first and second sections and an outer sleeve slidably disposed about the first and second sections. The first and second sections may define an annular groove positioned to receive the annular rim of the tubular base when the first and second sections are received about the flange. The tubular base may be secured to the first tubular member and the tubular extension may be secured to the second tubular member. The tubular base may be formed on an end of the first tubular member and the tubular extension is formed on an end of the second tubular member.

BRIEF DESCRIPTION OF THE DRAWINGS

Embodiments of the present disclosure are described herein with reference to the accompanying drawings, wherein:

FIG. 3 is a perspective side view of the adapter assembly of FIG. 1;

FIG. 4 is a perspective side view of the adapter assembly of FIG. 3 with the outer sleeve removed;

FIG. 5 is a perspective side view of the adapter assembly of FIGS. 3 and 4 with proximal and distal housings of first and second pusher assemblies removed;

FIG. 8 is an enlarged, perspective view of a coupling assembly and a transfer assembly of the adapter assembly of FIGS. 2-7;

FIG. 9 is a perspective side view of adapter assembly of FIGS. 2-7 with the housing assemblies removed;

FIG. 14 is an enlarged view of the indicated area of detail of FIG. 6;

FIG. 15 is an enlarged view of the indicated area of detail of FIG. 7;

FIG. 16 is an enlarged view of the indicated area of detail of FIG. 9;

FIG. 17 perspective side view of the extension assembly of FIG. 1;

FIG. 18 is a perspective side view of an inner flexible band assembly of the extension assembly of FIG. 17;

FIG. 19 is a perspective side view of an outer flexible band assembly of the extension assembly of FIG. 17;

FIG. 21 is a perspective side view of the inner and outer flexible band assemblies and frame assembly of FIG. 20;

FIG. 22 is an enlarged view of the indicated area of detail of FIG. 21;

FIG. 23 is a front, perspective view of the inner and outer flexible band assemblies and frame assembly of FIG. 20;

FIG. 24 is an enlarged view of the indicated area of detail of FIG. 23;

FIG. 30 is a perspective side view of the trocar assembly of FIG. 29;

FIG. 31 is a cross-sectional side view taken along line 31-31 of FIG. 30;

FIG. 43 is a cross-sectional side view taken along line 43-43 of FIG. 42;

FIG. 44 is a cross-sectional side view taken along line 44-44 of FIG. 42;

DETAILED DESCRIPTION OF EMBODIMENTS

Figure 1:
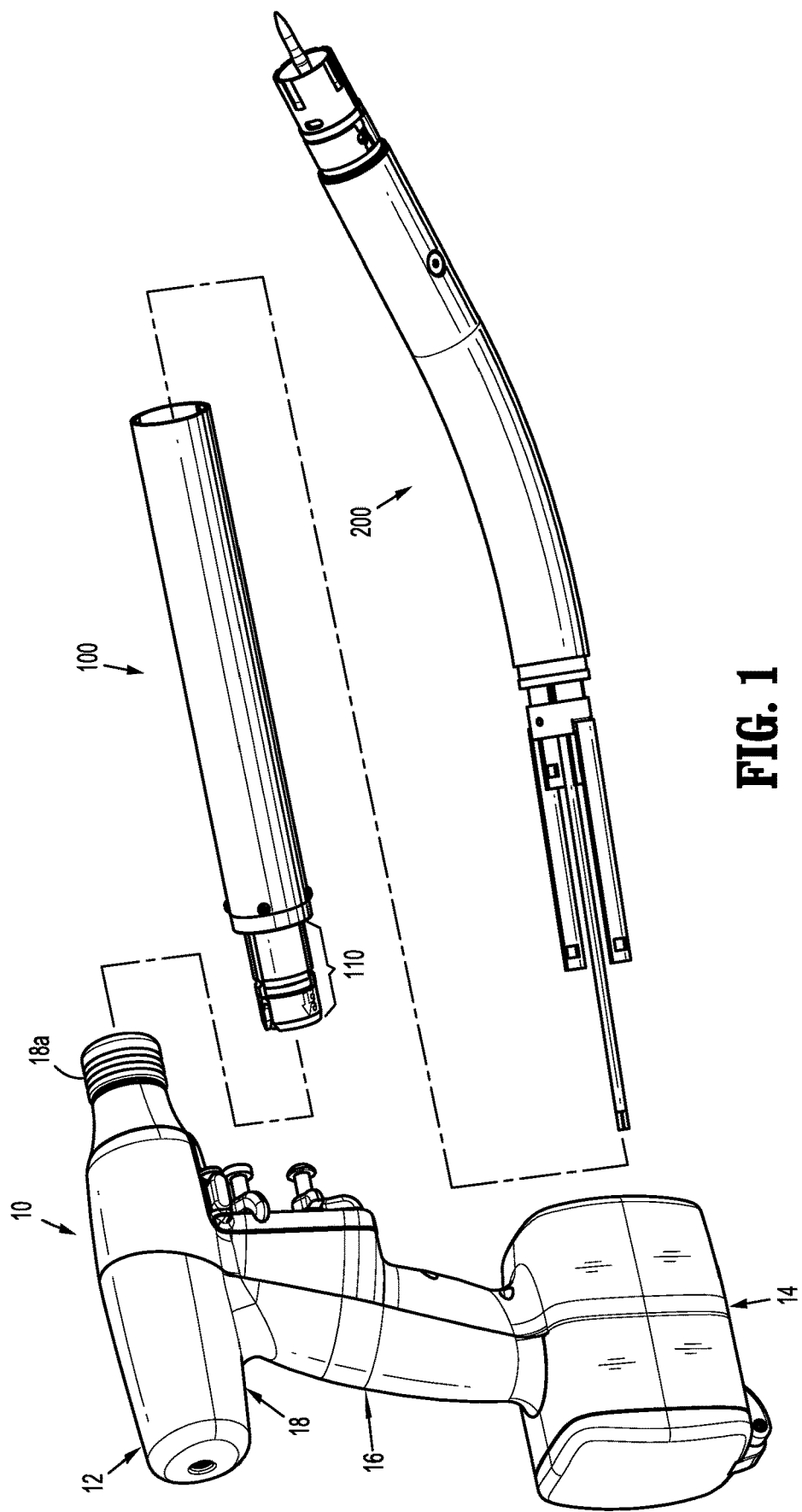
FIG. 1 is a perspective separated view of an adapter assembly, in accordance with an embodiment of the present disclosure, an extension assembly, in accordance with an embodiment of the present disclosure, and an exemplary electromechanical surgical device.

Embodiments of the presently disclosed adapter assemblies and extension assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as adapter assembly 100, and an extension assembly according to an embodiment of the present disclosure, shown generally as extension assembly 200, are configured for selective connection to a powered hand held electromechanical instrument shown, generally as surgical device 10. As illustrated in FIG. 1, surgical device 10 is configured for selective connection with adapter assembly 100, and, in turn, adapter assembly 100 is configured for selective connection with an extension assembly 200. Extension assembly 200 is configured for selective connection with a tool assembly or end effector, e.g. tool assembly 30 (FIG. 34), including a loading unit, e.g. loading unit 40 (FIG. 34), and an anvil assembly, e.g., anvil assembly 50 (FIG. 34), for applying a circular array of staples (not shown) to tissue (not shown).

Figure 2:
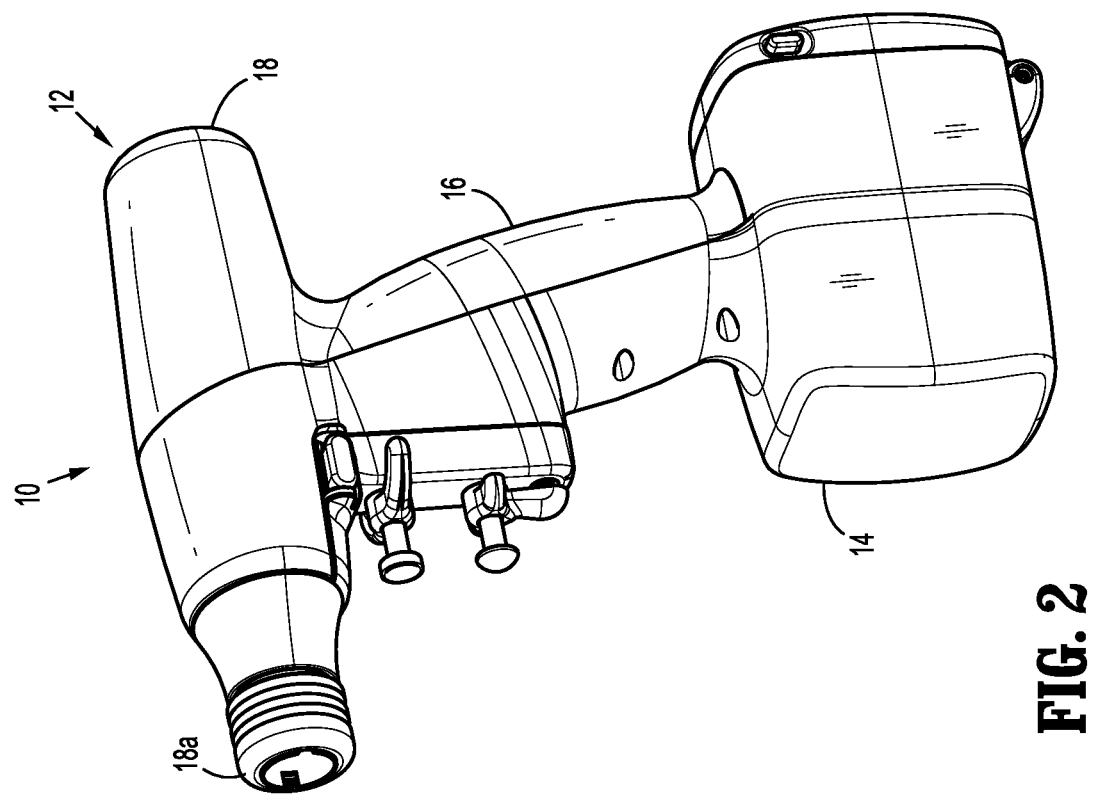
FIG. 2 is a perspective side view of the exemplary electromechanical surgical device of FIG. 1.
Figure 6:
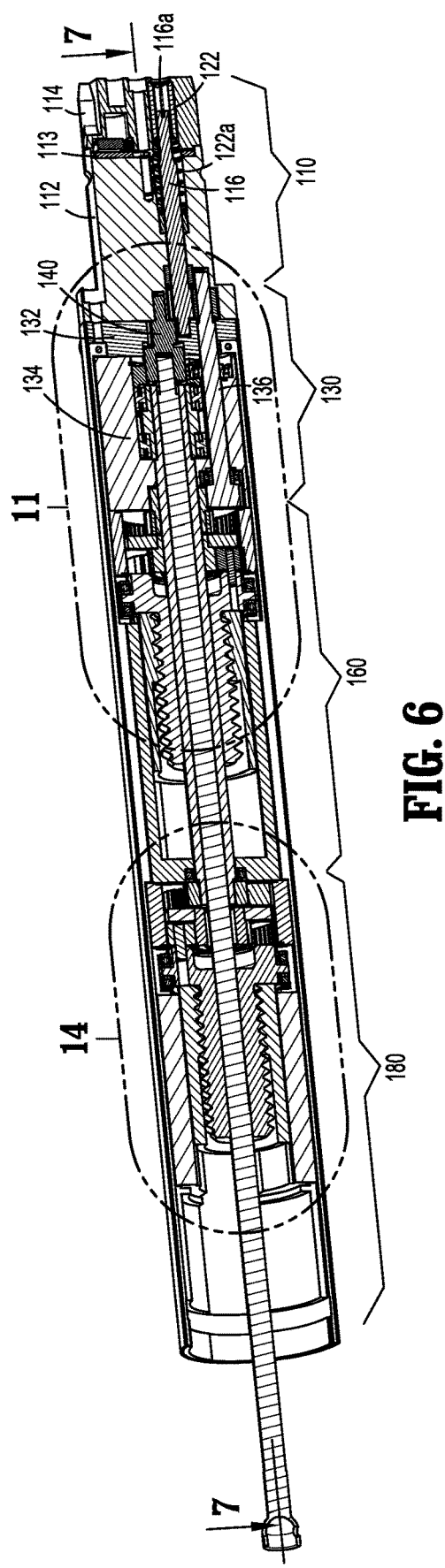
FIG. 6 is a cross-sectional side view of the adapter assembly of FIGS. 2-4 taken along line 6-6 in FIG. 3.
Figure 7:
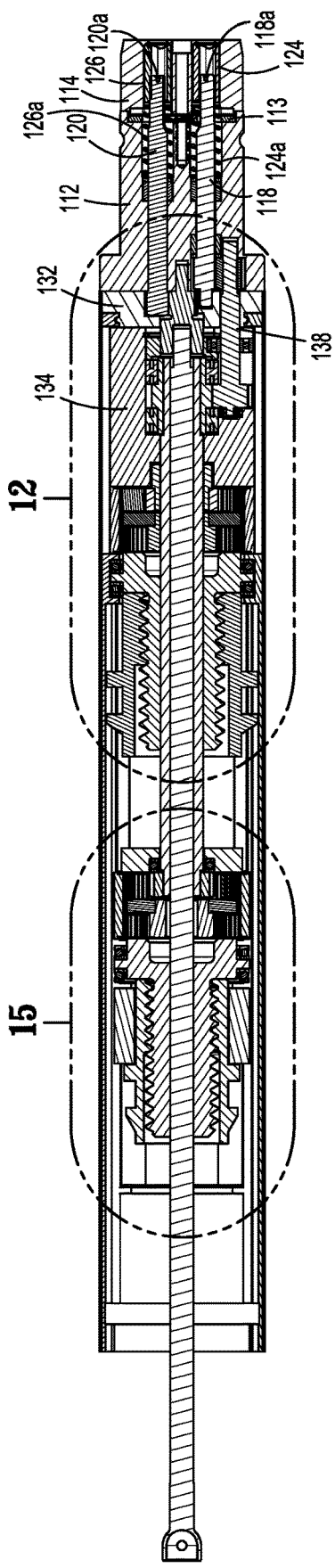
FIG. 7 is a cross-sectional side view of the adapter assembly of FIGS. 2-5 taken along line 7-7 in FIG. 5.

As illustrated in FIGS. 1 and 2, surgical device 10 includes a handle housing 12 having a lower housing portion 14, an intermediate housing portion 16 extending from and/or supported on lower housing portion 14, and an upper housing portion 18 extending from and/or supported on intermediate housing portion 16. A distal half-section of upper housing portion 18 defines a nose or connecting portion 18a configured to accept a corresponding drive coupling assembly 110 (FIG. 10) of adapter assembly 100. For a detailed description of the structure and function of an exemplary electromechanical instrument, please refer to commonly owned U.S. Pat. Appl. Publ. No. 2012/0253329 ("the '329 application"), the contents of which is incorporated by reference herein in its entirety.

Adapter assembly 100 will now be described with reference to FIGS. 3-20. Referring initially to FIG. 3, adapter assembly 100 includes a proximal end 102 configured for operable connection to connecting portion 18a (FIG. 1) of surgical device 10 (FIG. 1) and a distal end 104 configured for operable connection to extension assembly 200 (FIG. 1).

Turning to FIGS. 3-5, from proximal end 102 to distal end 104 of adapter assembly 100 includes a drive coupling assembly 110, a drive transfer assembly 130 operably connected to drive coupling assembly 110, a first pusher assembly 160 operably connected to drive transfer assembly 130, and a second pusher assembly 180 operably connected to drive transfer assembly 130. Each of drive transfer assembly 130, first pusher assembly 160 and second pusher assembly 180 are operably maintained within an outer sleeve 106 (FIG. 3). As will be described in further detail below, a shaft 108 (FIG. 3) extends longitudinally through adapter assembly 100 and is operably connected to drive transfer assembly 130.

With reference to FIGS. 5-9, drive coupling assembly 110 has a cylindrical profile and is configured to selectively secure adapter assembly 100 to surgical device 10 (FIG. 1). Drive coupling assembly 110 includes a connector housing 112 and a connector extension 114 fixedly connected to connector housing 112 by a mounting plate 113. Connector housing 112 and connector extension 114 operate to rotatably support a first rotatable proximal drive shaft 116, a second rotatable proximal drive shaft 118, and a third rotatable proximal drive shaft 120. Connector housing 112 and connector extension 114 of drive coupling assembly 110 also rotatably supports first, second, and third connector sleeves 116, 118, and 120, respectively. Each of connector sleeves 122, 124, 126 is configured to mate with respective first, second, and third drive connectors (not shown) of surgical device 10 (FIG. 1). Each connector sleeve 122, 124, 126 is further configured to mate with a proximal end 116a, 118a, 120a of respective first, second and third proximal drive shafts 116, 118, 120.

Drive coupling assembly 110 also includes first, second and third biasing members 122a, 124a and 126a disposed distally of respective first, second and third connector sleeves 122, 124, 126. Each of biasing ember 122a, 124a and 126a is disposed about respective first, second, and third rotatable proximal drive shafts 122, 124 and 126 to help maintain connector sleeves 122, 124, and 126 engaged with the distal end of respective drive rotatable drive connectors (not shown) of surgical device 10 when adapter assembly 100 is connect to surgical device 10. In particular, first, second and third biasing members 122a, 124a and 126a function to bias respective connector sleeves 122, 124 and 126 in a proximal direction.

For a detailed description of an exemplary drive coupling assembly, please refer to the '329 application, the contents of which was previously incorporated by reference herein.

With reference to FIGS. 9-13, drive transfer assembly 130 has a cylindrical profile and operably connects distal ends of first, second and third rotatable proximal drive shafts 116, 118 and 120 to shaft 108, first pusher assembly 160, and second pusher assembly 180, respectively. Drive transfer assembly 130 includes a support plate 132 (FIGS. 11 and 12) secured to a proximal end of connector housing 112 and a drive transfer housing 134 positioned adjacent support plate 132. Support plate 132 and housing 134 operate to rotatably support a first rotatable distal drive shaft 136, a second rotatable distal drive shaft 138 and a drive member 140.

First and second rotatable distal drive shafts 136 and 138 are each operably connected to respective first and second rotatable proximal drive shafts 116 and 118 of drive coupling assembly 110 by a pair of gears. In particular, distal ends of each of first and second rotatable proximal drive shaft 116 and 118 include a geared portion 142a and 144a, respectively, which engages a proximal drive gear 142b and 144b on a proximal end of respective first and second distal drive shafts 136 and 138. As shown, each of respective paired geared portion and proximal drive gear 142a, 142b and 144a, 144b are the same size to provide a 1:1 gear ratio between the respective rotatable proximal and distal drive shafts. In this manner, respective rotatable proximal and distal drive shafts rotate at the same speed. However, it is envisioned that either or both of the paired geared portions and proximal drive gears may be of different sizes to alter the gear ratio between the rotatable proximal and distal drive shafts.

A distal end of third proximal drive shaft 120 of drive coupling assembly 110 includes a geared portion 146a that engages a geared portion 146b formed on a proximal end of drive member 140 of drive transfer assembly 130. The size of geared portion 146a on third proximal drive shaft 120 and geared portion 146b on drive member 140 are the same size to provide a 1:1 gear ratio between third proximal drive shaft 120 and drive member 140. In this manner, third proximal drive shaft 120 and drive member 140 rotate at the same speed. However, it is envisioned that either or both of geared portions 146a, 146b may be of different sizes to alter the gear ratio between third proximal drive shaft 120 and drive member 140. A distal end of drive member 140 defines a socket 145 that receives a proximal end 108*a* of shaft 108. Alternatively, socket 145 may be configured to operably engage a proximal end 208*a* of a drive shaft (FIG. 17) of an extension assembly 200 (FIG. 17).

Drive transfer assembly 130 also includes a drive connector 148 (FIG. 11) operably connecting first rotatable distal drive shaft 136 to first pusher assembly 160 and a tubular connector 150 operably connecting second rotatable distal drive shaft 138 to second pusher assembly 180. In particular, a distal end of first rotatable distal drive shaft 136 includes a geared portion 152*a* that engages a geared portion 152*b* of drive connector 148. A distal end of second rotatable distal drive shaft 138 includes a geared portion 154*a* that engages a drive gear 154*b* secured to a distal end of tubular connector 150.

As shown, geared portion 152*a* of first rotatable distal drive shaft 136 is smaller than geared portion 152*b* of drive connector 148 to provide a gear ratio of greater than 1:1 between first rotatable distal drive shaft 136 and drive connector 148. In this manner, drive connector 148 rotates at a slower speed than first rotatable distal drive shaft 136. Similarly, geared portion 154*a* of second rotatable distal drive shaft 138 is smaller than drive gear 154*b* on tubular connector 150 to provide a gear ratio of greater than 1:1 between second rotatable distal drive shaft 138 and drive connector 148. In this manner, tubular connector 150 rotates at a slower speed than second rotatable distal drive shaft 138. However, it is envisioned that each of paired geared portion 152*a* and geared portion 152*b*, and geared portion 154*a* and drive gear 154*b* may be the same size to provide a gear ratio of 1:1 between respective first rotatable distal drive shaft 136 and drive connector 148 and between second rotatable distal drive shaft 138 and tubular connector 150.

Figure 10:
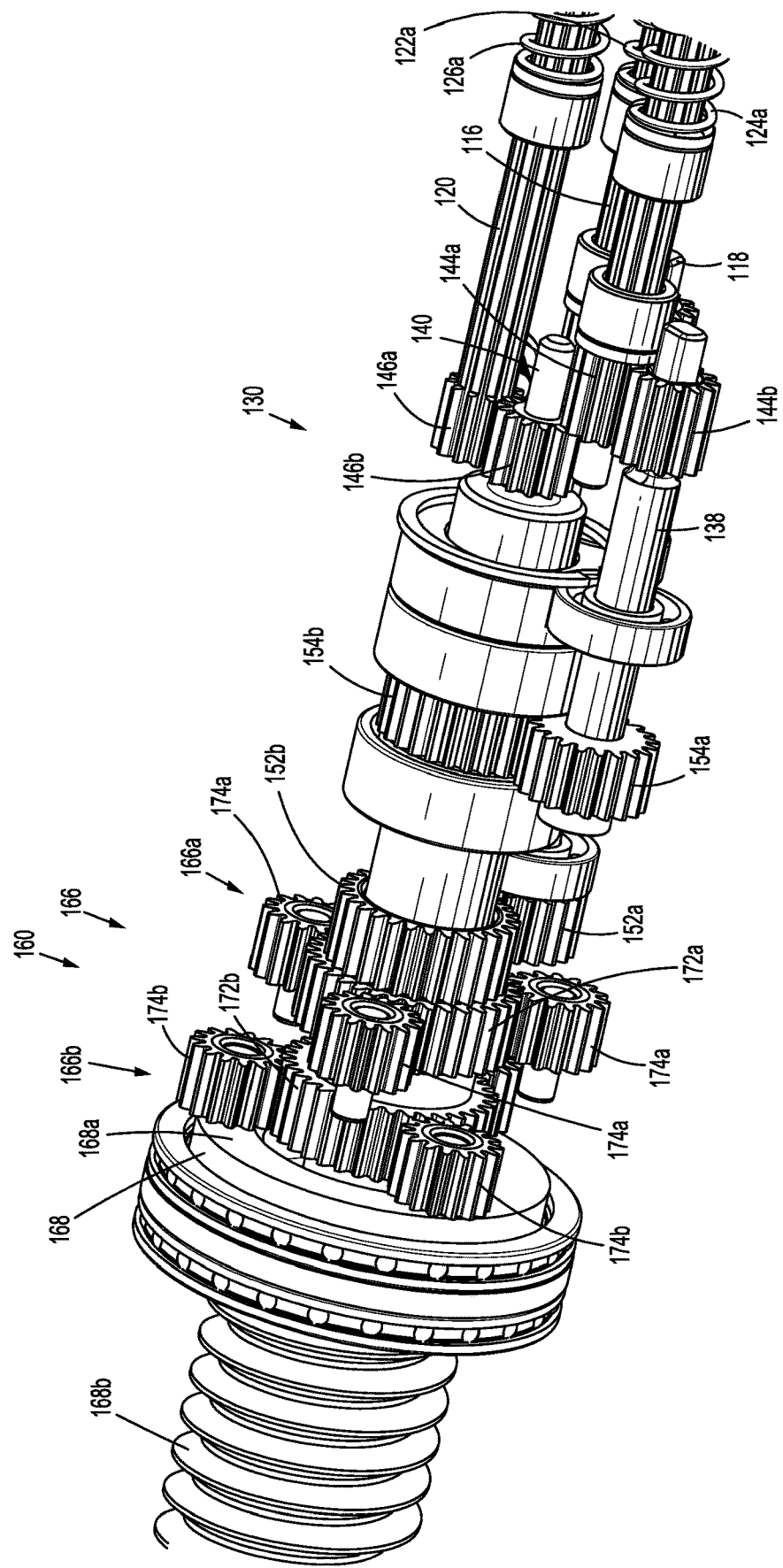
FIG. 10 is an enlarged view of the indicated area of detail of FIG. 9.
Figure 11:
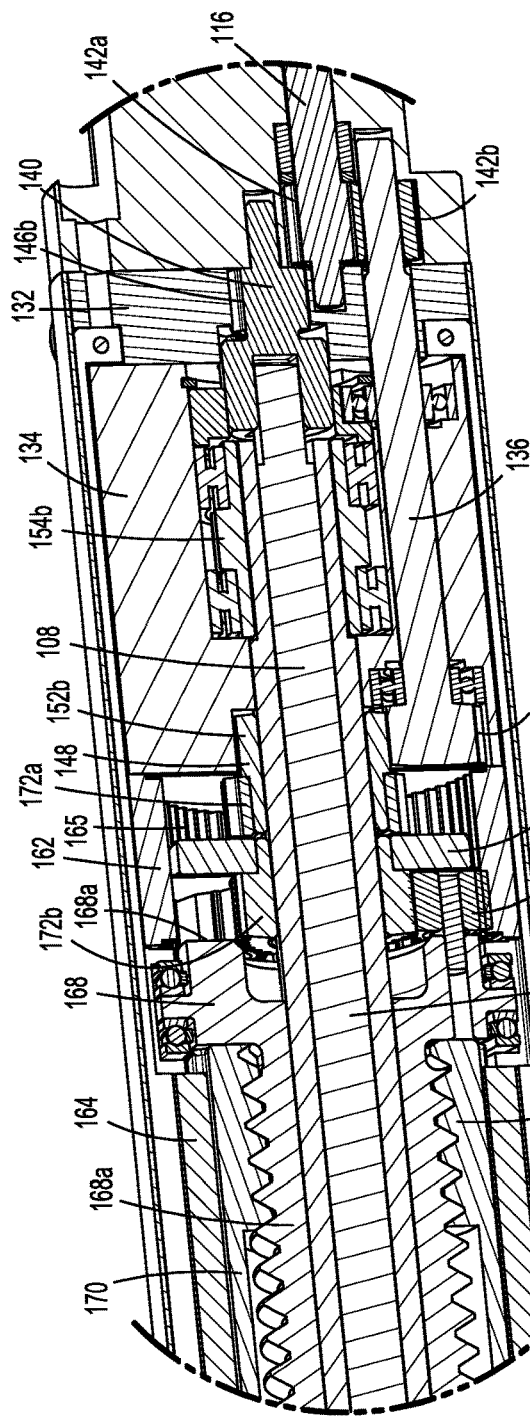
FIG. 11 is an enlarged view of the indicated area of detail of FIG. 6.

With particular reference to FIGS. 9-13, first pusher assembly 160 includes proximal and distal housing sections 162, 164 (FIG. 11), a planetary gear assembly 166 operably mounted within proximal housing section 162, a screw member 168 (FIG. 11) operably connected to planetary gear assembly 166 and rotatably supported within distal housing section 164, and a pusher member 170 (FIG. 11) operably connected screw member 168 and slidably disposed within distal housing section 164. Proximal housing section 162 includes a pair of longitudinal flanges 162*a* (FIG. 4; only one shown) and distal housing section 164 includes a pair of longitudinally flattened portions 164*a*. Each of the flanges 162*a* and the flattened portions 164*a* of respective proximal and distal housing sections 162, 164 engage an inner surface of sleeve 106 to prevent rotation of respective proximal housing section 162 and distal housing section 164 relative to sleeve 106 during operation of surgical device 10. Planetary gear assembly 166 includes first and second planetary gear systems 166*a*, 166*b* (FIG. 10). First planetary gear system 166*a* includes a central drive gear 172*a* mounted on a distal end of drive connector 148 of drive transfer assembly 130 and a plurality of planetary gears 174*a* rotatably mounted to a rotatable support ring 176.

Each planetary gear 174*a* engages central drive gear 172*a* and a toothed inner surface 165 of proximal housing section 162. As central drive gear 172*a* rotates in a first direction, i.e., clockwise, each planetary gear 174*a* rotates in a second direction, i.e., counter-clockwise. As each planetary gear 174*a* rotates in the second direction, engagement of planetary gears 174*a* with toothed inner surface 165 of distal housing section 162 causes rotatable support ring 176 to rotate in the first direction. Conversely, rotation of central drive gear 172*a* in the second direction causes rotation of each planetary gear 174*a* in the first direction thereby causing rotation of rotatable support ring 176 in the second direction. The configuration of first planetary gear system 166*a* provides a reduction in the gear ratio. In this manner, the speed of rotation of rotatable support ring 174 is less than the speed of rotation of central drive gear 172*a*.

Second planetary gear system 166*b* includes a central drive gear 172*b* securely affixed to rotatable support ring 176 and a plurality of planetary gears 174*b* rotatably mounted to a proximal end surface 168*a* of screw member 168. Each planetary gear 174*b* engages central drive gear 172*b* and toothed inner surface 165 of proximal housing section 162. As rotatable support ring 176 of first planetary gear system 166*a* rotates in the first direction thereby causing central drive gear 172*b* to also rotate in the first direction, each planetary gear 174*b* rotates in the second direction. As each planetary gear 174*b* rotates in the second direction, engagement of planetary gears 174*b* with toothed inner surface 165 of proximal housing section 162 causes screw member 168 to rotate in the first direction. Conversely, rotation of central drive gear 172*b* in the second direction causes rotation of each planetary gear 174*b* in the first direction, thereby causing screw member 168 to rotate in the second direction. The configuration of second planetary gear system 166*b* provides a reduction in the gear ratio. In this manner, the speed of rotation of screw member 168 is less than the speed of rotation of central drive gear 172*b*. First and second planetary gear systems 166*a*, 166*b* operate in unison to provide a reduction in the gear ratio between first rotatable proximal drive shaft 116 and screw member 168. In this manner, the reduction in the speed of rotation of screw member 168 relative to drive connector 148 is a product of the reduction provided by the first and second planetary gear systems 166*a*, 166*b*.

Screw member 168 is rotatably supported within proximal housing portion 162 and includes a threaded distal end 168*b* that operably engages a threaded inner surface 170*a* of pusher member 170. As screw member 168 is rotated in the first direction, engagement of threaded distal end 168*b* of screw member 168 with threaded inner surface 170*a* of pusher member 170 causes longitudinal advancement of pusher member 170, as indicated by arrows "A" in FIG. 12. Conversely, rotation of screw member 168 in the second direction causes retraction of pusher member 170.

Pusher member 170 includes a pair of tabs 178 formed on a distal end thereof for engaging connector extensions 240, 242 (FIG. 19) of outer flexible band assembly 230 (FIG. 19) of extension assembly 200 (FIG. 17). Although shown as tabs 178, it is envisioned that pusher member 170 may include any structure suitable for selectively engaging connector extensions 240, 242 of outer flexible band 230 of extension assembly 200.

With particular reference now to FIGS. 14-16, second pusher assembly 180 is substantially similar to first pusher assembly 160, and includes proximal and distal housing sections 182, 184, a planetary gear assembly 186 operably mounted within proximal housing section 182, a screw member 188 operably connected to planetary gear assembly 186 and rotatably supported within distal housing section 184, and a pusher member 190 operably connected to screw member 188 and slidably disposed within distal housing section 184. Each of proximal housing section 182 and distal housing section 184 includes a pair of longitudinal flanges 182*a*, 184*a* (FIG. 4; only one shown), respectively, engage an inner surface of sleeve 106 of adapter assembly 100 to prevent rotation of respective proximal housing section 182 and distal housing section 184 relative to sleeve 106 during operation of surgical device 10. Planetary gear assembly 186 includes first and second planetary gear systems 186a, 186b (FIG. 16). First planetary gear system 186a includes a central drive gear 192a mounted on a distal end of tubular connector 150 of drive transfer assembly 130 and a plurality of planetary gears 194a rotatably mounted to a rotatable support ring 196.

Each planetary gear 194a engages central drive gear 192a and a toothed inner surface 185 of proximal housing section 182. As central drive gear 192a rotates in a first direction, i.e., clockwise, each planetary gear 194a rotates in a second direction, i.e., counter-clockwise. As each planetary gear 194a rotates in the second direction, engagement of planetary gears 194a with toothed inner surface 185 of distal housing section 182 causes rotatable support ring 196 to rotate in the first direction. Conversely, rotation of central drive gear 192a in the second direction causes rotation of each planetary gear 194a in the first direction thereby causing rotation of rotatable support ring 196 in the second direction. The configuration of first planetary gear system 186a provides a reduction in the gear ratio. In this manner, the speed of rotation of rotatable support ring 194 is less than the speed of rotation of central drive gear 190a.

Second planetary gear system 186b includes a central drive gear 192b securely affixed to rotatable support ring 196 and a plurality of planetary gears 194b rotatably mounted to a proximal end surface 188a of screw member 188. Each planetary gear 194b engages central drive gear 192b and toothed inner surface 185 of proximal housing section 182. As rotatable support ring 196 of first planetary gear system 186a rotates in the first direction thereby causing central drive gear 192b to also rotate in the first direction, each planetary gear 174b rotates in the second direction. As each planetary gear 194b rotates in the second direction, engagement of planetary gears 194b with toothed inner surface 185 of proximal housing section 182 causes screw member 188 to rotate in the first direction. Conversely, rotation of central drive gear 192b in the second direction causes rotation of each planetary gear 194b in the first direction, thereby causing screw member 198 to rotate in the second direction. The configuration of second planetary gear system 186b provides a reduction in the gear ratio. In this manner, the speed of rotation of screw member 188 is less than the speed of rotation of central drive gear 182b. First and second planetary gear systems 186a, 186b operate in unison to provide a reduction in the gear ratio between second rotatable proximal drive shaft 118 and screw member 188. In this manner, the reduction in the speed of rotation of screw member 188 relative to tubular connector 150 is a product of the reduction provided by the first and second planetary gear systems 186a, 186b.

Screw member 188 is rotatably supported within proximal housing portion 182 and includes a threaded distal end 188b that operably engages a threaded inner surface 190a of pusher member 190. As screw member 188 is rotated in the first direction, engagement of threaded distal end 188b of screw member 188 with threaded inner surface 190a of pusher member 190 causes longitudinal advancement of pusher member 190. Conversely, rotation of screw member 188 in the second direction causes retraction of pusher member 190. Pusher member 190 includes a pair of longitudinal flanges 191 (FIG. 5; only one shown) that engage distal housing section 184 of second pusher assembly 180 for preventing rotation of pusher member 190 relative distal housing section 184.

Pusher member 190 includes a pair of tabs 198 formed on a distal end thereof for engaging connector extensions 220, 224 (FIG. 18) of inner flexible band assembly 210 (FIG. 18) of extension assembly 200 (FIG. 17). Although shown as tabs 198, it is envisioned that pusher member 190 may include any structure suitable for selectively engaging connector extensions 240, 242 of outer flexible band 230 of extension assembly 200.

Extension assembly 200 for operably connecting adapter assembly 100 (FIG. 3) with a circular loading unit, e.g. loading unit 40 (FIG. 34) and an anvil assembly, e.g., anvil assembly 50 (FIG. 34) will be described with reference now to FIGS. 17-34. In particular, a proximal end 202 of extension assembly 200 operably connects with distal end 104 (FIG. 3) of adapter assembly 100 (FIG. 3) and a distal end 204 of extension assembly 200 operably connects with loading unit 40 and anvil assembly 50. As shown, extension assembly 200 provides a slight curvature between proximal and distal end 202, 204. In alternative embodiment, extension assembly 200 may be straight or may include a greater curvature. Although extension assembly 200 will be shown and described as being used to connect loading unit 40 and anvil assembly 50 to adapter assembly 100 (FIG. 3), it is envisioned that the aspects of the present disclosure may be modified for use with various loading units, anvil assemblies, and adapter assemblies. Exemplary loading units and anvil assemblies are described in commonly owned U.S. Pat. No. 8,590,763 and U.S. patent application Ser. Nos. 14/056,301 and Ser. No.14/149,355, the contents of each being incorporated herein by reference in their entirety.

Extension assembly 200 includes an inner flexible band assembly 210 (FIG. 18), about an outer flexible band assembly 230 (FIG. 19) slidably disposed about inner flexible band assembly 210, a frame assembly 250 (FIG. 20) for supporting inner and outer flexible band assemblies 210, 230, a trocar assembly 270 (FIG. 29) operably received through inner and outer flexible band assemblies 210, 230, and a connector assembly 290 for securing loading unit 40 (FIG. 34) to extension assembly 200. An outer sleeve 206 (FIG. 17) is received about frame assembly 250 and trocar assembly 270 and inner and outer flexible band assemblies 210, 230 are slidably received through outer sleeve 206. As will be described in further detail below, extension assembly 200 may include a drive shaft 208 operably connected to trocar assembly 270 and extending through proximal end 202 of extension assembly 200.

With reference to FIG. 18, inner flexible band assembly 210 includes first and second inner flexible bands 212, 214, a support ring 216, a support base 218, and first and second connection extensions 220, 222. Proximal ends 212a, 214a of respective first and second inner flexible bands 212, 214 are laterally spaced apart and securely attached to support ring 216. Distal ends 212b, 214b of first and second inner flexible bands 212, 214 are laterally spaced apart and securely attached to a proximal end 218a of support base 218. Each of first and second inner flexible bands 212, 214 may be attached to support ring 216 and/or support base 218 in any suitable manner, including, for example, by press-fitting, welding, adhesives, and/or with mechanical fasteners. As will be described in further detail below, inner flexible band assembly 210 is configured to be slidably received about trocar assembly 270 (FIG. 28) and within outer flexible band assembly 230 (FIG. 19) and outer sleeve 206 (FIG. 17).

First and second connection extensions 220, 222 of inner flexible band assembly 210 extend proximally from support ring 216 and operably connect inner flexible band assembly 210 with pusher member 190 (FIG. 15) of second pusher assembly 180 (FIG. 15) of adapter assembly 100 (FIG. 3).

In particular, each of first and second connection extensions 220, 222 define openings 221, 223 configured to receive tabs 198 (FIG. 15) of pusher member 190 (FIG. 15) of second pusher assembly 180. Receipt of tabs 198 of pusher member 190 within openings 221, 223 of respective first and second extensions 220, 222 secure inner flexible band assembly 210 of extension assembly 200 with second pusher assembly 180 of adapter assembly 100. First and second connection extensions 220, 222 may be integrally formed with support ring 216, or attached thereto in any suitable manner.

Figure 34:
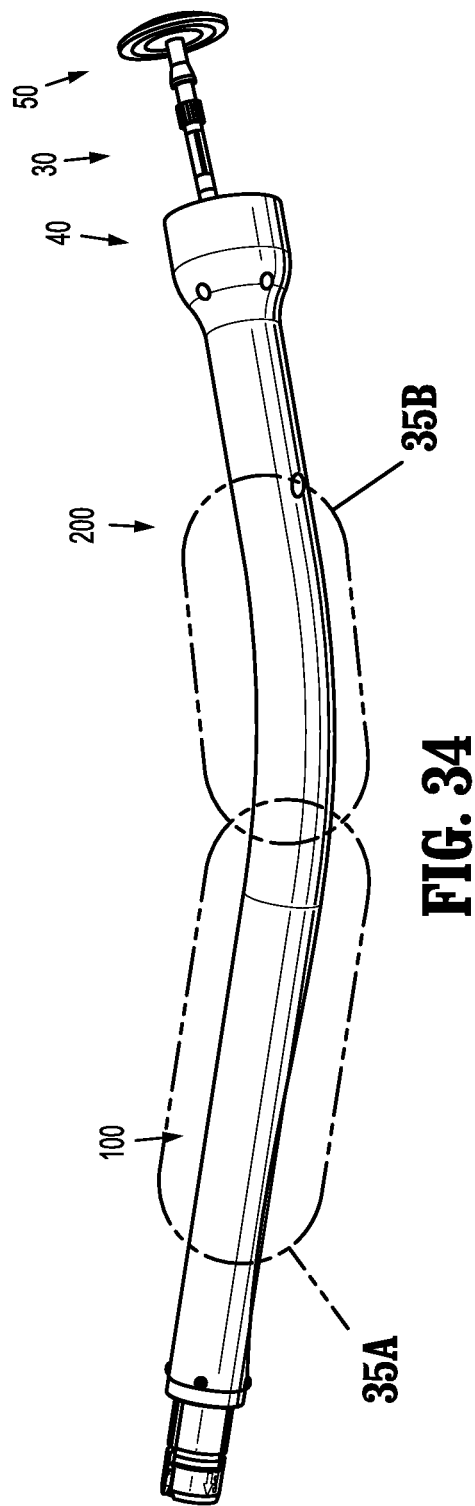
FIG. 34 is a perspective side view of the adapter assembly of FIG. 3 connected to the extension assembly of FIG. 17 and an end effector and an anvil assembly connected to the extension assembly.

Support base 218 extends distally from inner flexible bands 212, 214 and is configured to selectively connect extension assembly 200 with loading unit 40 (FIG. 34). Specifically, a distal end 218b 218a of support base 218 includes a flange 224 for operable engagement with an axially movable assembly (not shown) of loading unit 40 (FIG. 34). In one embodiment, flange 224 is configured for connection with a knife assembly (not shown) of loading unit 40 (FIG. 34).

With reference now to FIG. 19, outer flexible band assembly 230 is substantially similar to inner flexible band assembly 210 and includes first and second flexible bands 232, 234 laterally spaced and connected on proximal ends 232a, 234a to a support ring 236 and on distal ends 232b, 234b to a proximal end 238a of a support base 238. Each of first and second outer flexible bands 232, 234 may be attached to support ring 236 and support base 238 in any suitable manner, including, for example, by press-fitting, welding, adhesives, and/or with mechanical fasteners. As will be described in further detail below, outer flexible band assembly 230 is configured to receive trocar assembly 270 (FIG. 28) therethrough.

First and second connection extensions 240, 242 of outer flexible band assembly 230 extend proximally from support ring 236 and operably connect outer flexible band assembly 230 with pusher member 170 (FIG. 12) of first pusher assembly 160 (FIG. 12) of adapter assembly 100 (FIG. 1). In particular, each of first and second connection extensions 240, 242 define openings 241, 243 configured to receive tabs 178 (FIG. 12) of pusher member 170 of first pusher assembly 180. Receipt of tabs 178 of pusher member 170 within openings 241, 243 of respective first and second extensions 240, 242 secures outer flexible band assembly 230 of extension assembly 200 with first pusher assembly 180 of adapter assembly 100. First and second connection extensions 240, 242 may be integrally formed with support ring 236, or attached thereto in any suitable manner.

Support base 238 extends distally from outer flexible bands 232, 234 and is configured to selectively connect extension assembly 200 with loading unit 40 (FIG. 34). Specifically, a distal end 238b of support base 238 includes a flange 244 for operable engagement with an axially movable assembly (not shown) of a loading unit (not shown). In one embodiment, flange 244 is configured for connection with a staple pusher assembly (not shown) of loading unit 40 (FIG. 34).

With reference now to FIGS. 20-26, frame assembly 250 includes first and second proximal spacer members 252, 254, and first and second distal spacer members 256, 258. When secured together, first and second proximal spacer members 252, 254 define a pair of inner longitudinal slots 253a for slidably receiving first and second flexible bands 212, 214 (FIG. 18) of inner flexible band assembly 210 (FIG. 18) and a pair of outer longitudinal slots 253b for slidably receiving first and second flexible bands 232, 234 (FIG. 19) of outer flexible band assembly 230 (FIG. 19).

First and second proximal spacer members 252, 254 further define a longitudinal passage 255 for receipt of trocar assembly 270.

In one embodiment, and as shown, first and second proximal spacer members 252, 254 are formed of plastic and are secured together with a snap-fit arrangement. Alternatively, first and second proximal spacer members 252, 254 may be formed of metal or other suitable material and may be secured together in any suitable manner, including by welding, adhesives, and/or using mechanical fasteners.

First and second distal spacer members 256, 258 define a pair of inner slots 257a for slidably receiving first and second flexible bands 212, 214 (FIG. 18) of inner flexible band assembly 210 (FIG. 18) and a pair of outer slots 257b for slidably receiving first and second flexible bands 232, 234 (FIG. 19) of outer flexible band assembly 230 (FIG. 19). First and second distal spacer members 256, 258 further define a longitudinal passage 259 for receipt of trocar assembly 270.

Figure 26:
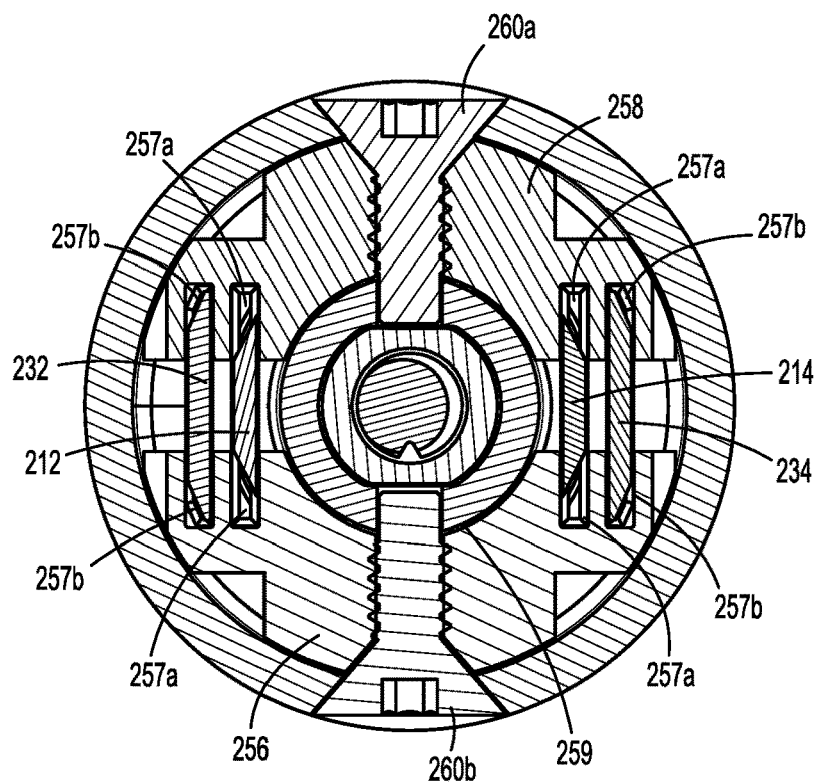
FIG. 26 is a cross-sectional end view taken along line 26-26 of FIG. 17.

In one embodiment, and as shown, each of first and second distal spacer members 256, 258 are secured about inner and outer flexible band assemblies 210, 230 and to outer sleeve 206 (FIG. 17) by a pair of screws 260a, 260b (FIG. 26). Alternatively, first and second distal spacer members 256, 258 may be secured together in any suitable manner, including by welding, adhesives, and/or using mechanical fasteners. First and second distal spacer members 256, 258 may be formed of metal or any other suitable material.

Figure 27:
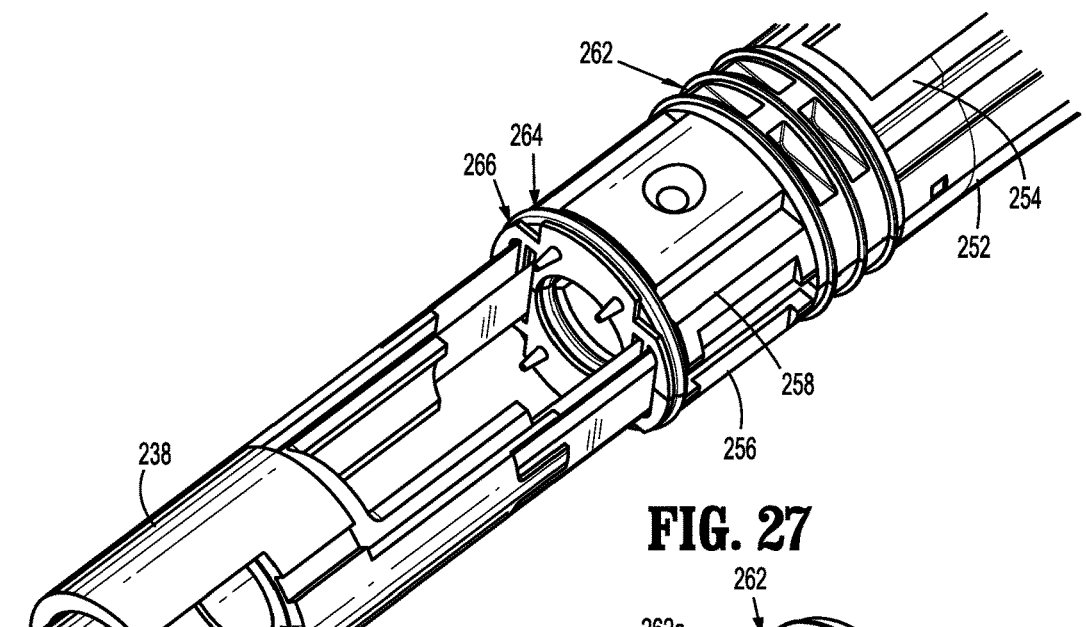
FIG. 27 is an enlarged perspective side view of a distal end of the inner and outer flexible band assemblies and frame assembly of FIG. 20 including a proximal seal member and first and second distal seal members.
Figure 28:
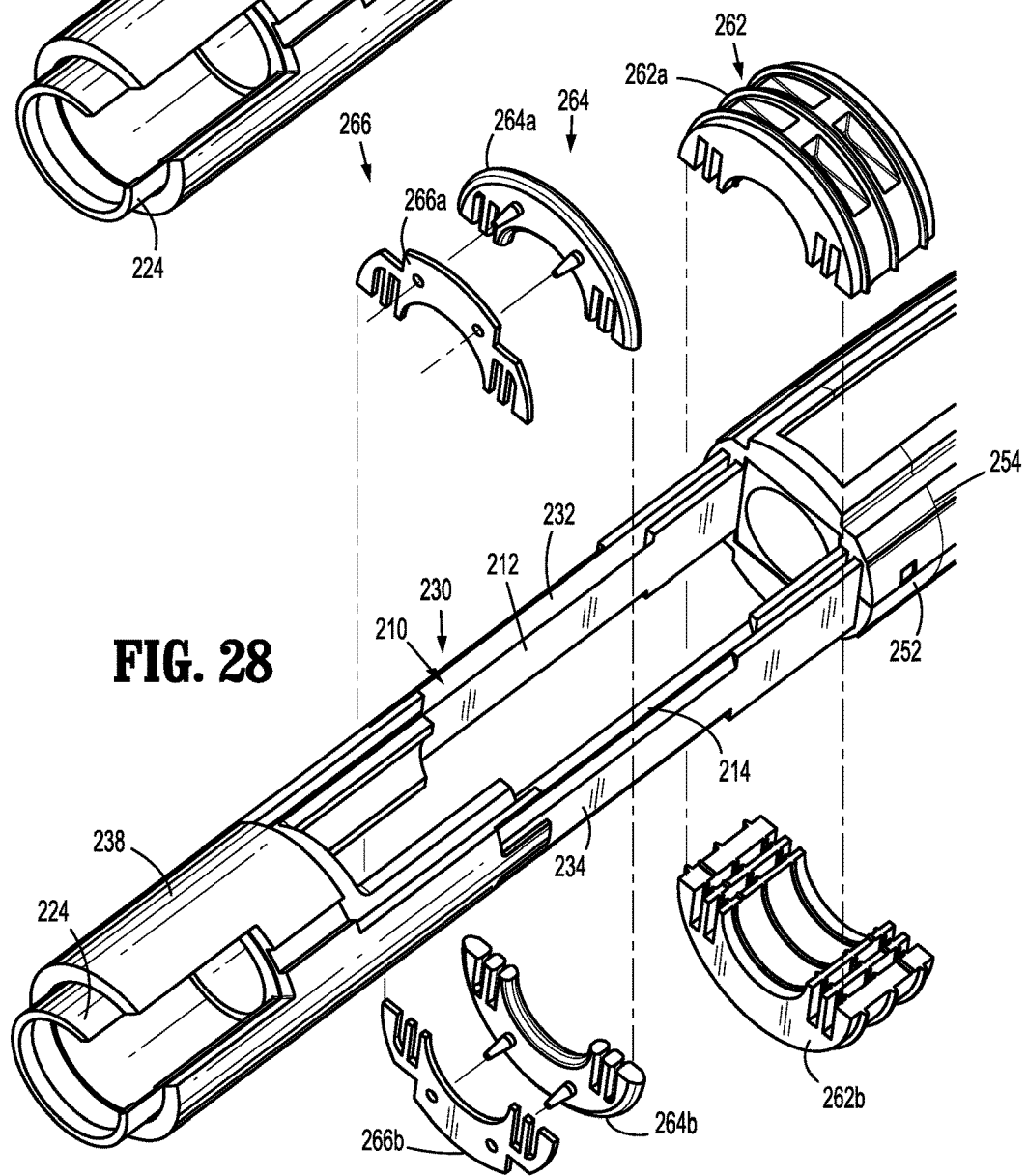
FIG. 28 is an exploded perspective view of the proximal seal member and first and second distal seal members of FIG. 27.

With reference now to FIGS. 27 and 28, frame assembly 250 further includes a proximal seal member 252 and first and second distal seal members 264, 266. Each of proximal seal member 252 and first and second distal seal members 264, 266 include seals halves 262a, 262b, 264a, 264b, 266a, 266b, respectively. Proximal seal member 262 is received between first and second proximal spacer members 252, 254 and first and second distal spacer members 256, 258. First half 264a of first distal seal member 264 is secured to first half 266a of second distal seal member 266 and second half 264b of first distal seal member 264 is secured to second half of second distal seal member 266. Proximal seal member 262 and first and second distal seal members 264, 266 engage outer sleeve 206 (FIG. 17), inner and outer flexible bands 212, 214 and 232, 234 of respective inner and outer flexible band assemblies 210, 230 and trocar assembly 270 (FIG. 28) in a sealing manner. In this manner, proximal seal member 262 and first and second distal seal members 264, 266 operate to provide a fluid tight seal between distal end 204 and proximal end 202 of extension assembly 200.

With reference to FIGS. 29-32, trocar assembly 270 of extension assembly 200 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion 273 which engages a threaded distal portion 276b of drive screw 276. As drive screw 276 is rotated within trocar member 274, engagement of inner threaded portion 273 of trocar member 274 with threaded distal portion 276b of drive screw 276 causes longitudinal movement of trocar member 274 within outer housing 272 of trocar assembly 270. Rotation of drive screw 276 in a first direction causes longitudinal advancement of trocar member 274 and rotation of drive screw 276 in a second direction causes longitudinal retraction of trocar member 274. A distal end 274b of trocar member 274 is configured to selectively engage anvil assembly 50 (FIG. 34).

A bearing assembly 278 is mounted to a proximal end 272a of outer housing 272 of trocar assembly 270 for rotatably supporting a proximal end 276a of drive screw 276 relative to outer housing 272 and trocar member 274. Bearing assembly 278 includes a housing 278a, proximal and distal spacers 278b, proximal and distal retention clips 278c, proximal and distal bearings 278d, and a washer 278e. As shown, proximal end 276a of drive screw 276 includes a flange 276c for connection with a link assembly 280.

Figure 12:
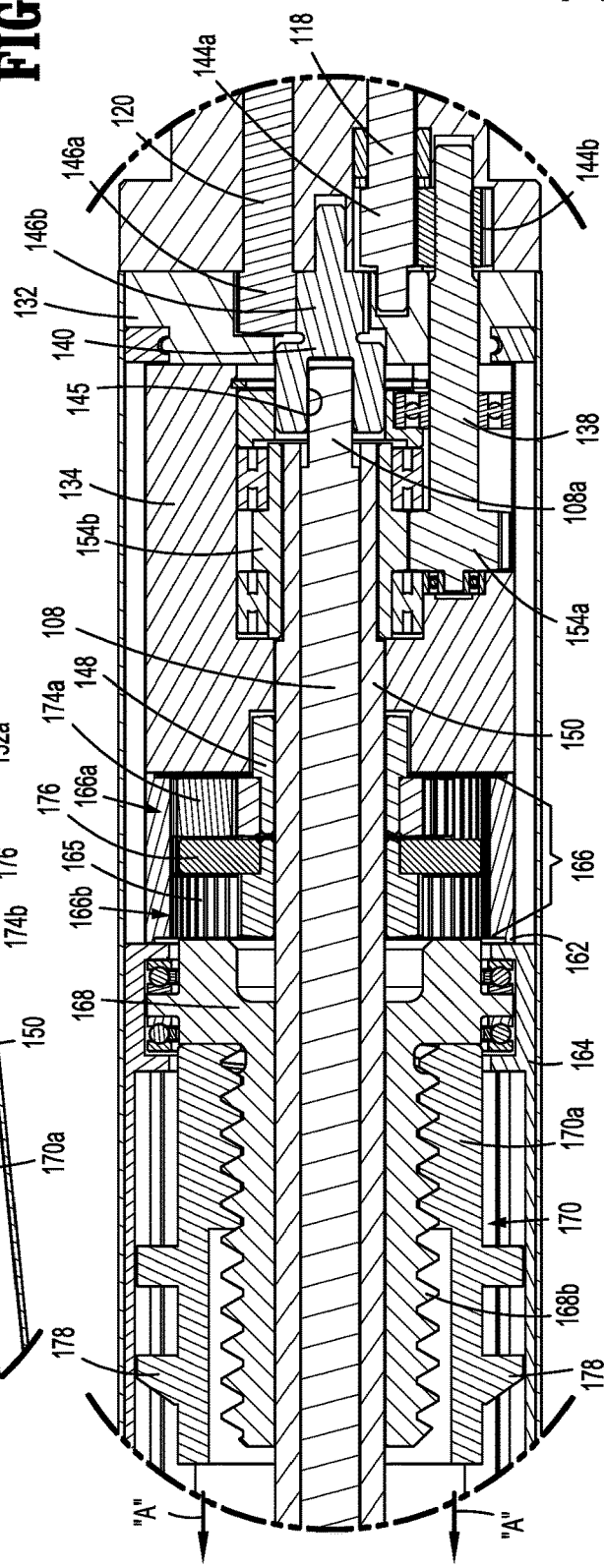
FIG. 12 is an enlarged view of the indicated area of detail of FIG. 7.
Figure 13:
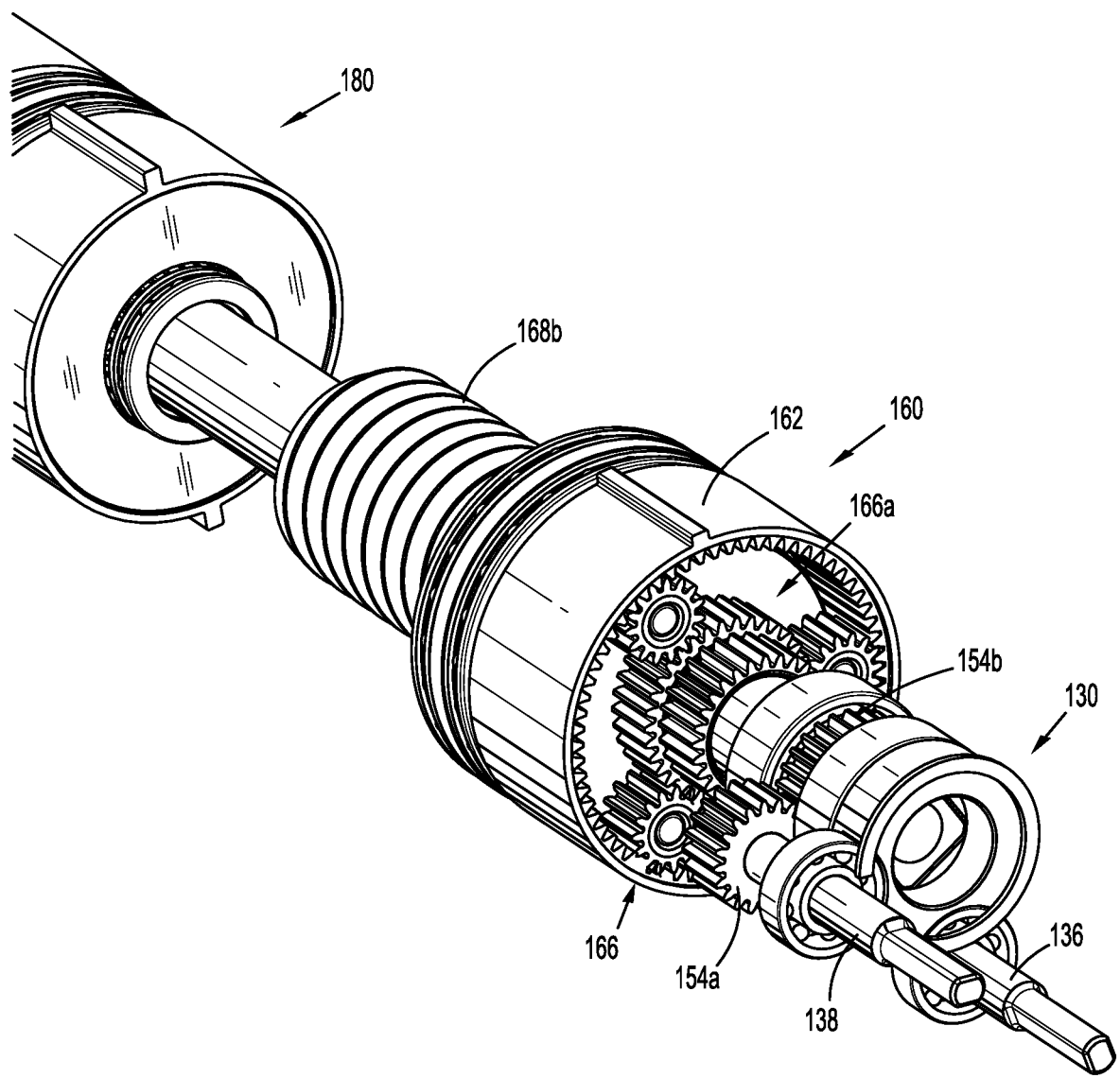
FIG. 13 is a perspective end view of the transfer assembly of FIG. 8.
Figure 20:
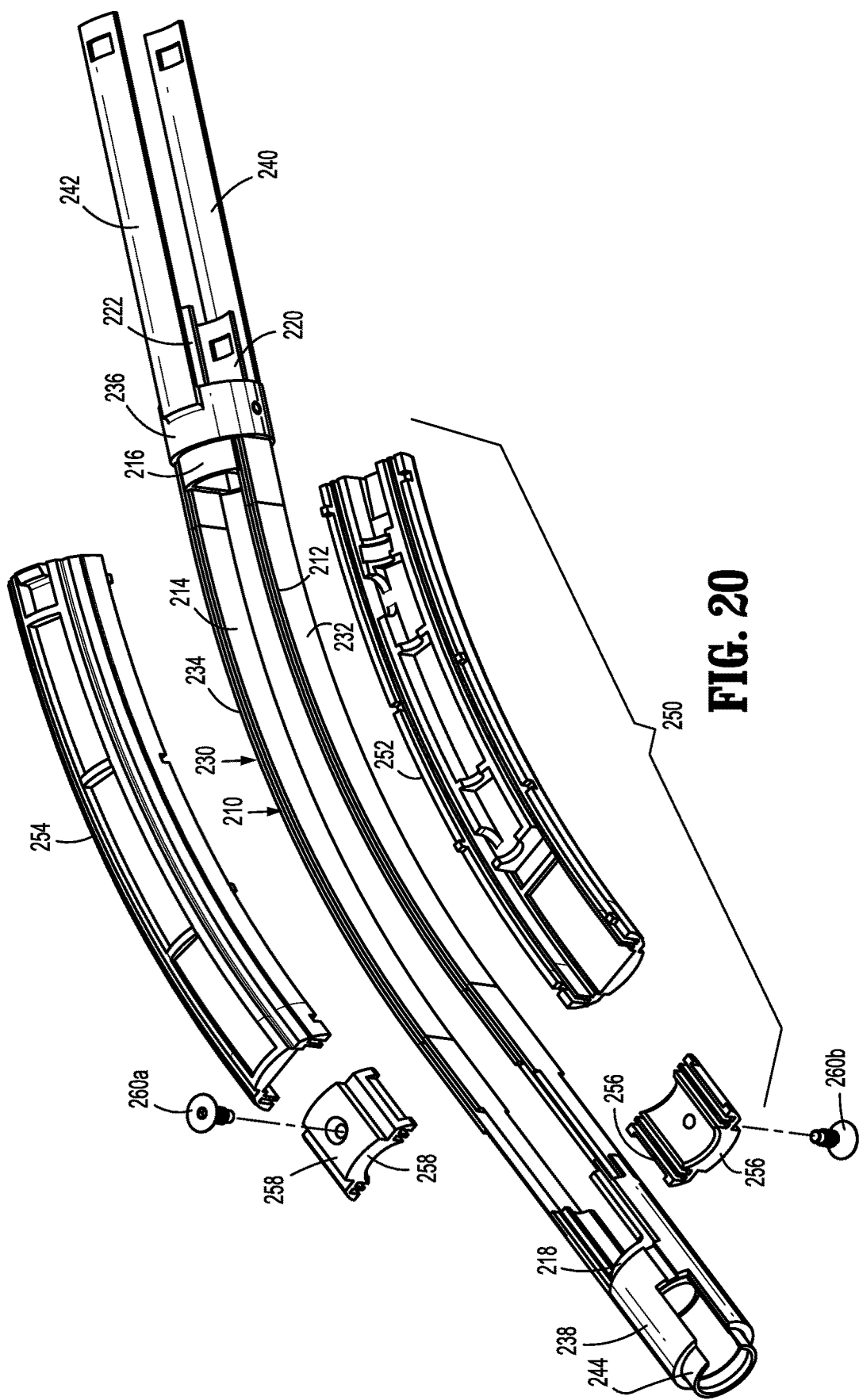
FIG. 20 is a perspective side view of the inner and outer flexible band assemblies of FIGS. 18 and 19 and an exploded view of a frame assembly of the extension assembly of FIG. 17.
Figure 25:
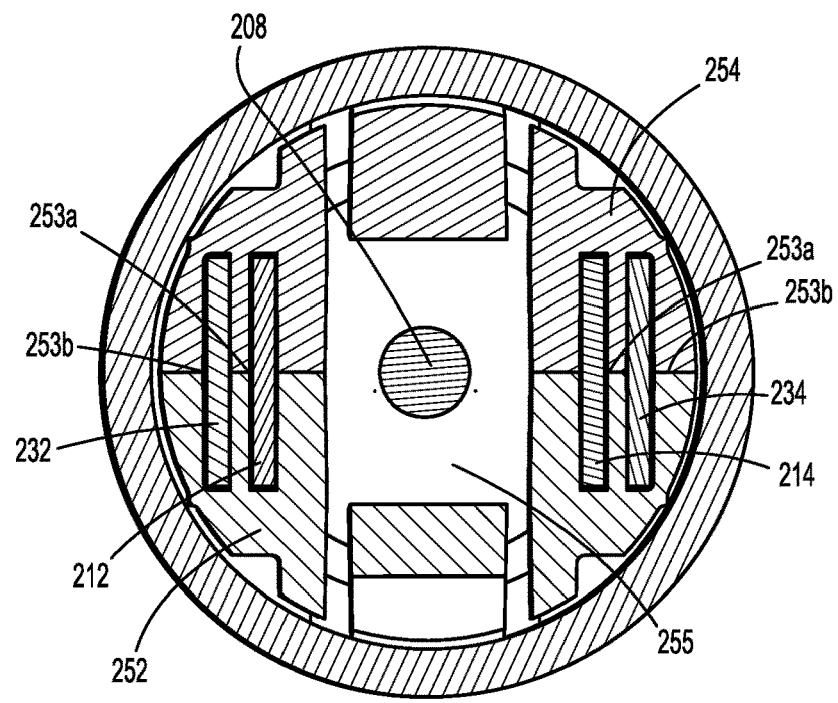
FIG. 25 is a cross-sectional end view taken along line 25-25 of FIG. 17.
Figure 29:
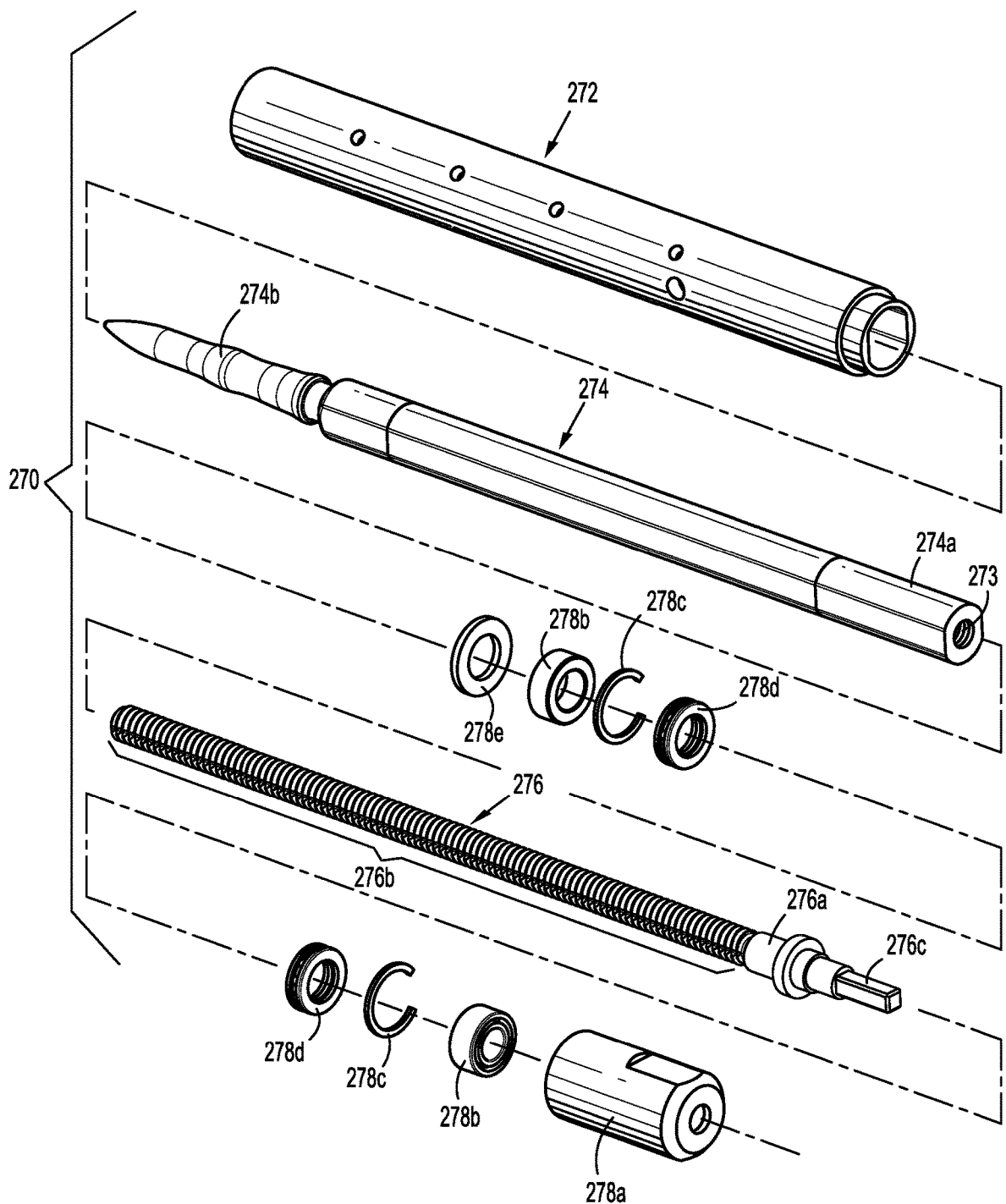
FIG. 29 is an exploded view of a trocar assembly of the extension assembly of FIG. 17.
Figure 29A:
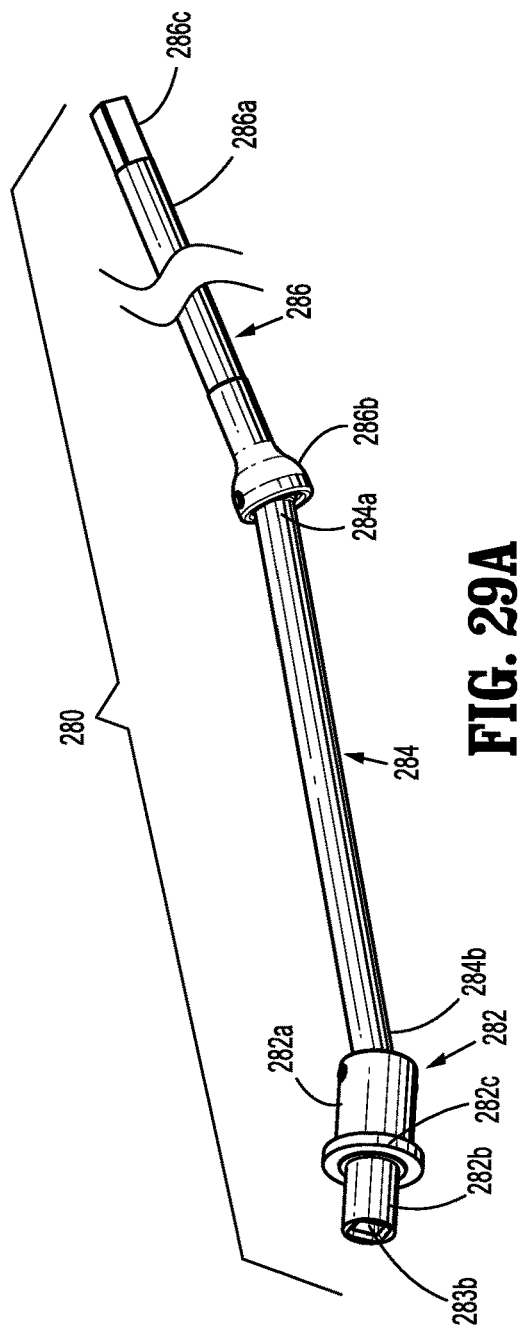
FIG. 29A is a perspective side view of a link assembly of the extension assembly of FIG. 17.
Figure 32:
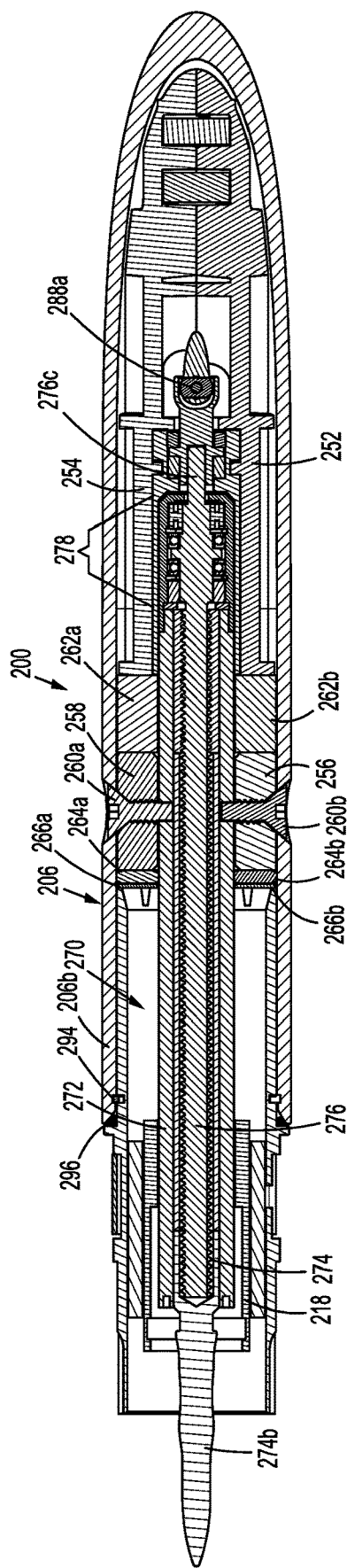
FIG. 32 is a cross-sectional top view taken along line 32-32 of FIG. 17.

Link assembly 280 operably connects transfer assembly 130 (FIG. 6) of adapter assembly 100 with trocar assembly 270 (FIG. 30) of extension assembly 200. More particularly, link assembly 280 transfers rotational energy from drive member 140 (FIG. 6) of transfer assembly 130 of adapter assembly 100 through the curved outer tube 206 (FIG. 17) of extension assembly 200 to flange 276c (FIG. 29) on proximal end 276a of drive screw 276 of trocar assembly 270 of extension assembly 200. with reference to FIGS. 29A and 29B, link assembly 280 includes a coupling member 282, a first drive shaft 284, and a second drive shaft 286. A proximal end 282a of coupling member 282 defines a recess 283a for receiving a distal end 284b of first drive shaft 284. A distal end 282b of coupling member 282 defines a recess 283a for operably receiving flange 276c on proximal end 276a of drive screw 276. Coupling member 282 includes an annular flange 282c for rotatably receiving coupling member 282 between first and second proximal spacer members 252, 254 (FIG. 32). Proximal and distal ends 284a, 284 of first drive shaft 284 define oversized openings 285a, 285b, respectively, for receiving pins 288a, 288b, respectively. A distal end 286b of second drive shaft 286 defines a recess 287 for operably receiving proximal end 284a of drive shaft 284. A proximal end 286a of drive shaft 286 includes a flange 286c for operable receipt within socket 145 of drive member 140 of drive transfer assembly 130 of adapter assembly 100 (FIG. 12).

Figure 29B:
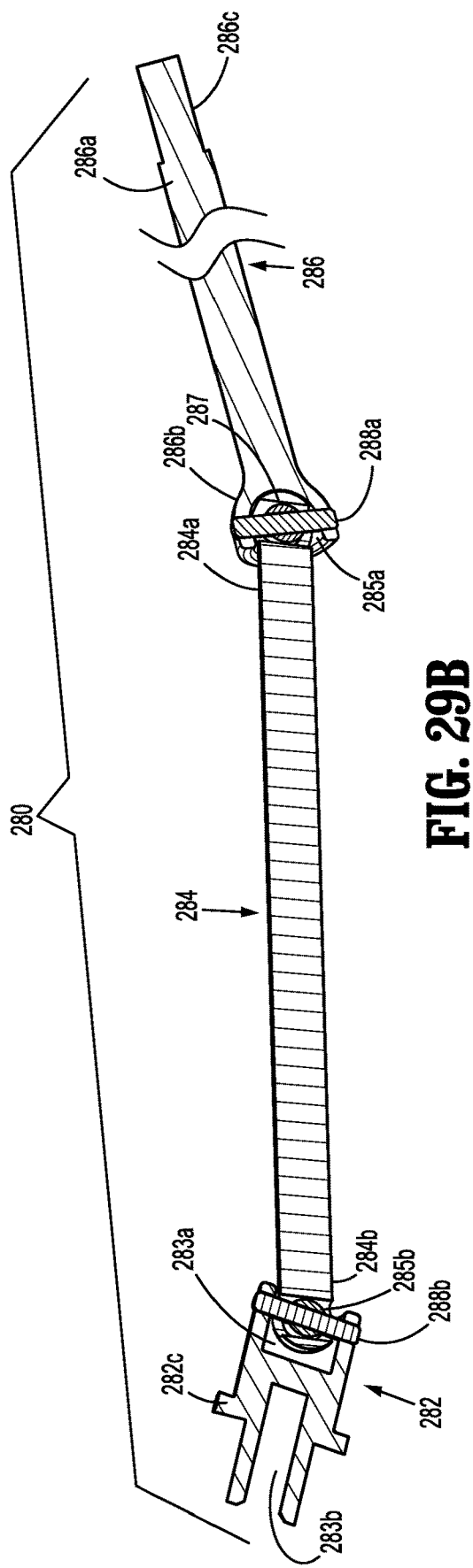
FIG. 29B is a cross-sectional side view of the link assembly of FIG. 29A.

With particular reference to FIG. 29B, proximal end 284a of first drive shaft 284 is operably received within recess 287 in distal end 286b of second drive shaft 286. Distal end 284b of first drive shaft 284 is pivotally secured within recess 283a of coupling member 282 by pin 288a received through oversized opening 285b in distal end 284b of first drive shaft 284. Proximal end 284a of first drive shaft 284 is pivotally secured within recess 287 in distal end 286b of second drive shaft 286 by pin 288b received through oversized opening 285a in proximal end 284a of first drive shaft 284. Recesses 283a and 287 of coupling member 282 and second drive shaft 286, respectively, and oversized openings 285a, 285b of first drive shaft 284 are configured to permit pivoting of second drive shaft 286 relative to first drive shaft 284 and pivoting of first drive shaft 284 relative to coupling member 282 as each of first and second drive shaft 284, 286, and coupling member 282 are rotated about their respective longitudinal axes to transfer rotational force from transfer assembly 130 (FIG. 6) of adapter assembly 100 to trocar assembly 270 (FIG. 30) of extension assembly 200.

Figure 33:
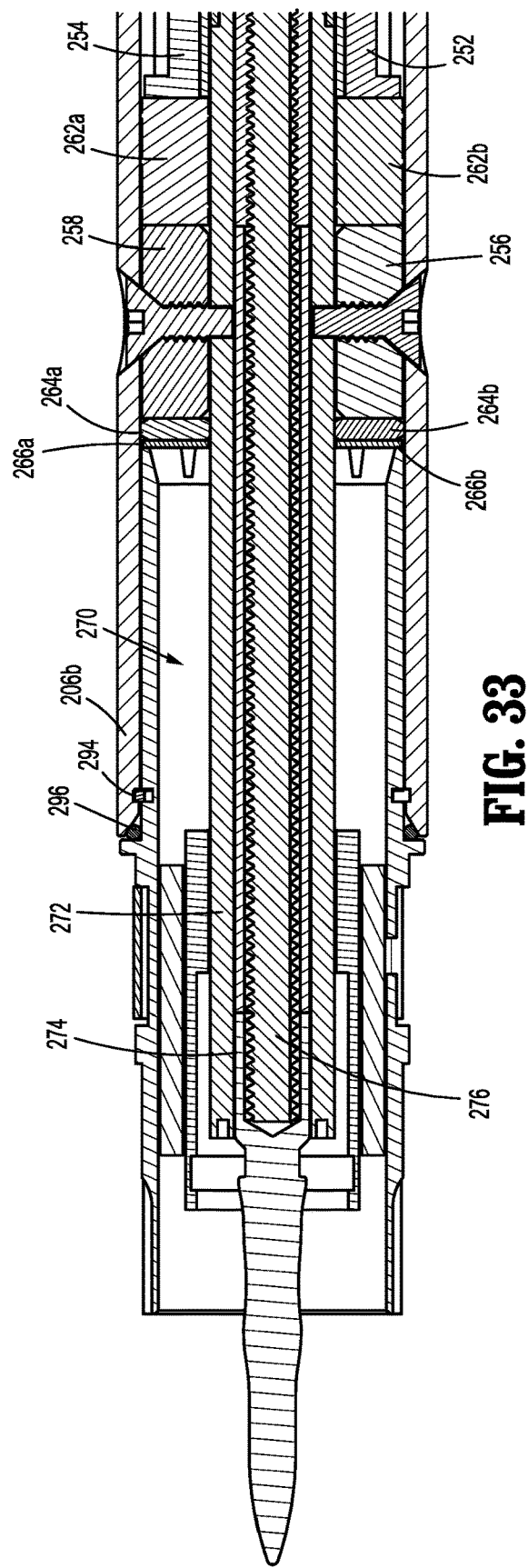
FIG. 33 is an enlarged cross-sectional view of the distal end of the extension assembly of FIG. 17.

With reference now to FIGS. 32 and 33, connector assembly 290 of extension assembly 200 includes a tubular connector 292 attached to a distal end 206b of outer sleeve 206 and about distal ends of inner and outer flexible assemblies 210, 230 (FIG. 26) and trocar assembly 270. In particular, a proximal end 292a of tubular connector 292 is received within and securely attached to distal end 206b of outer sleeve 206 by a retaining clip 294. An O-ring 296 forms a fluid tight seal between tubular connector 292 of connector assembly 290 and outer sleeve 206. A distal end 292b of tubular connector 292 is configured to selectively engage a proximal end of loading unit 40 (FIG. 34). Distal end 292b of tubular connector 292 engages the circular loading unit with a snap-fit arrangement, bayonet coupling, or in another suitable manner.

Figure 35A:
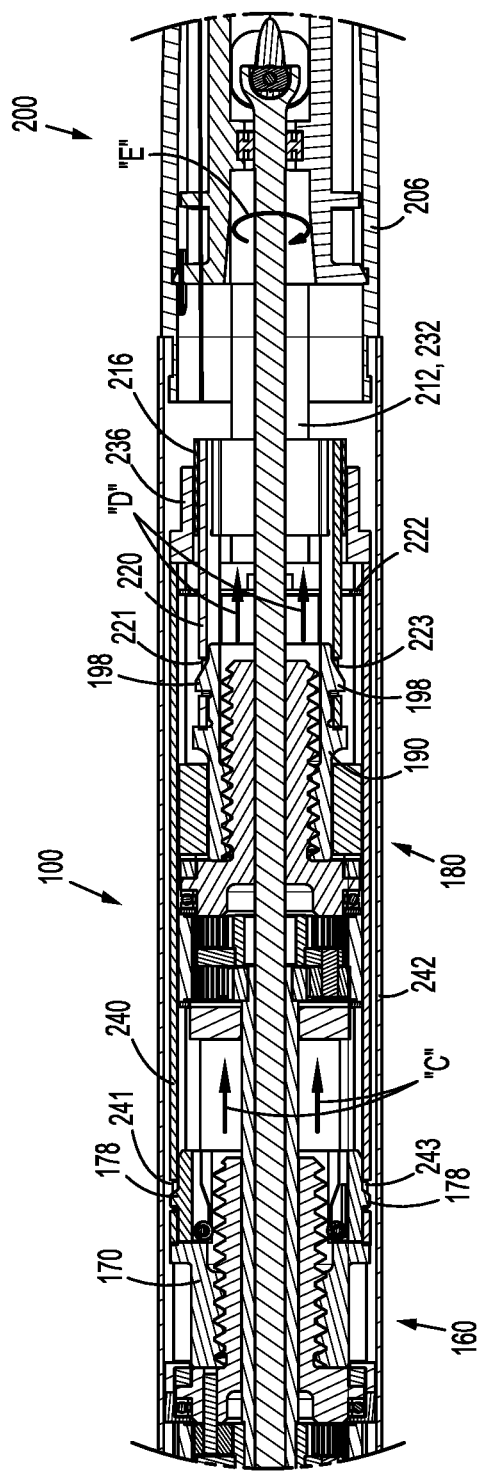
FIG. 35A is an enlarged cross-sectional top view of the indicated area of detail of FIG. 34.
Figure 35B:
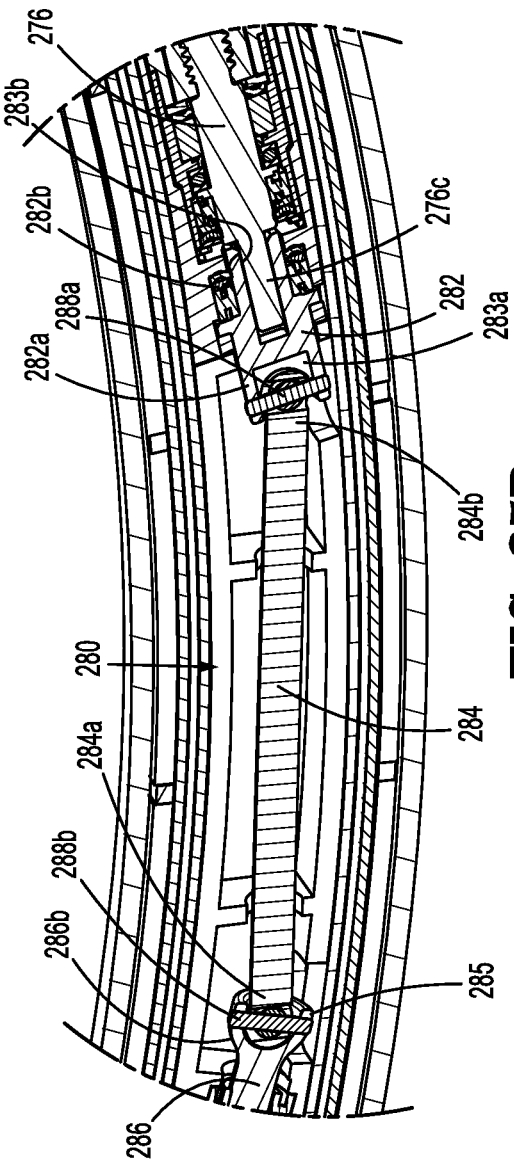
FIG. 35B is an enlarged cross-sectional side view of the indicated area of detail in FIG. 34.
Figure 36:
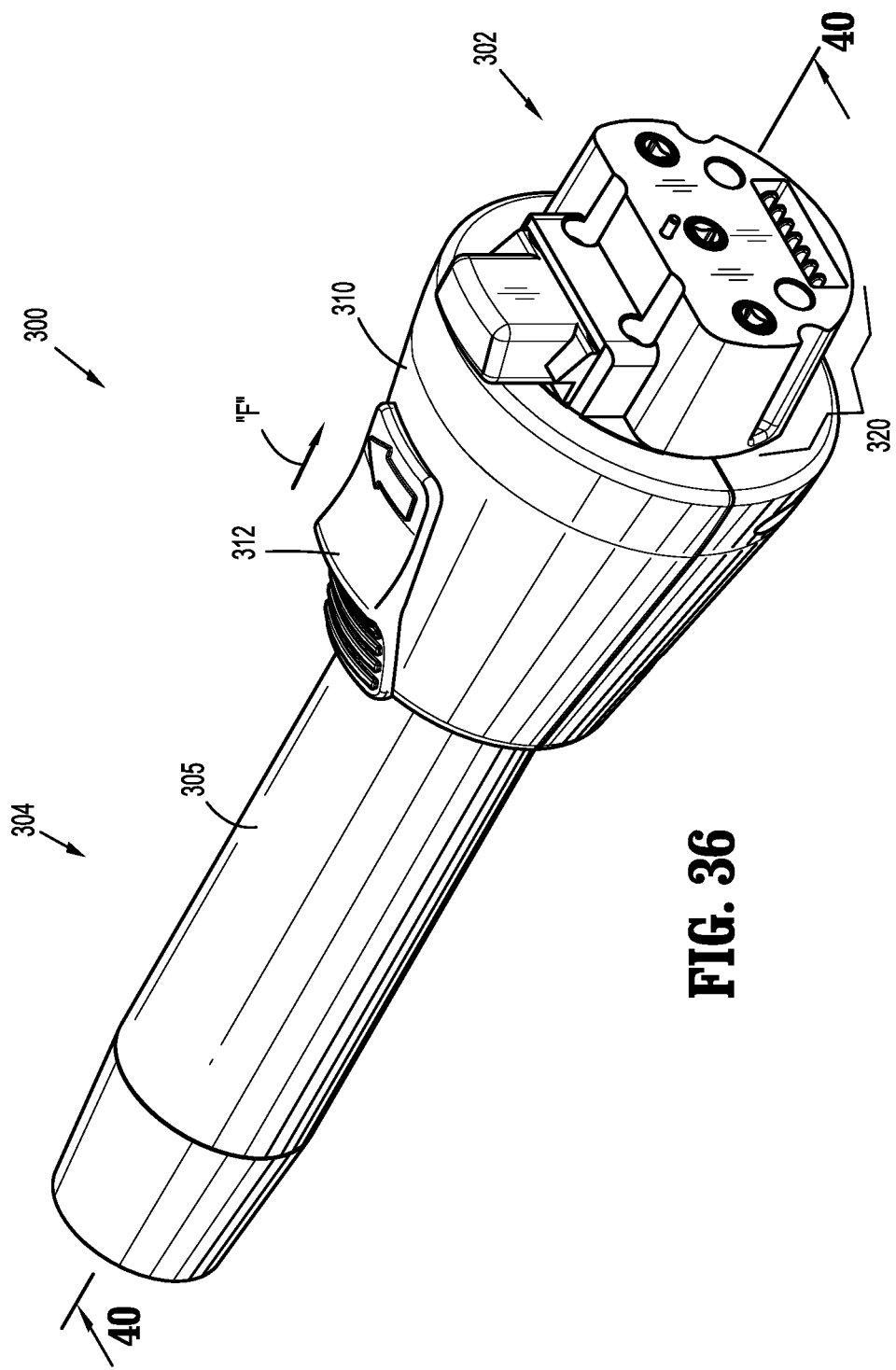
FIG. 36 is a rear, perspective view of an adapter assembly according to another embodiment of the present disclosure.
Figure 37:
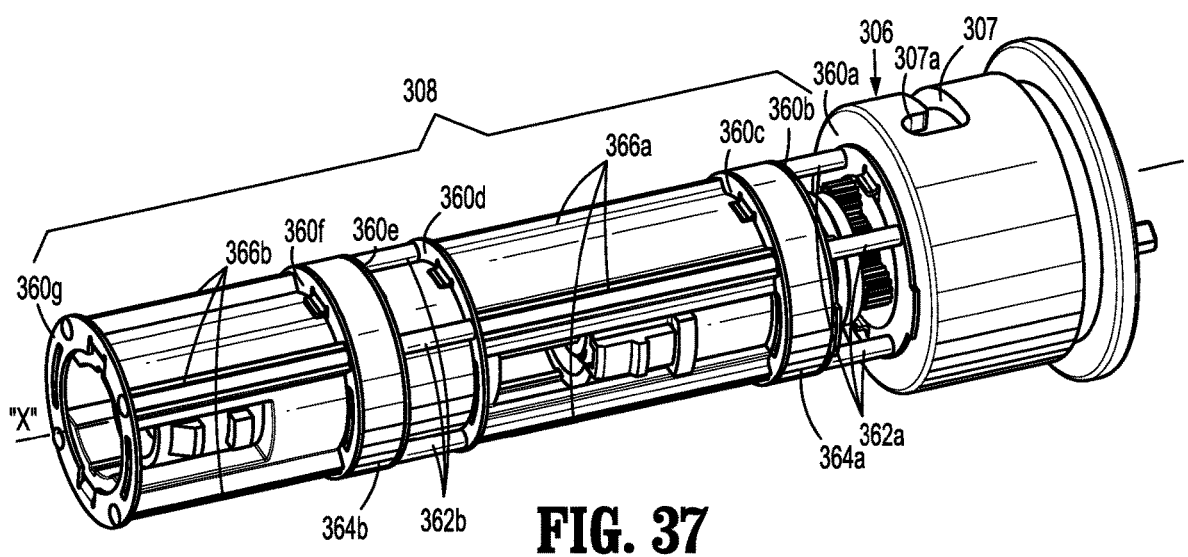
FIG. 37 is a perspective side view of the adapter assembly of FIG. 36 with an outer sleeve and a handle member removed.
Figure 38:
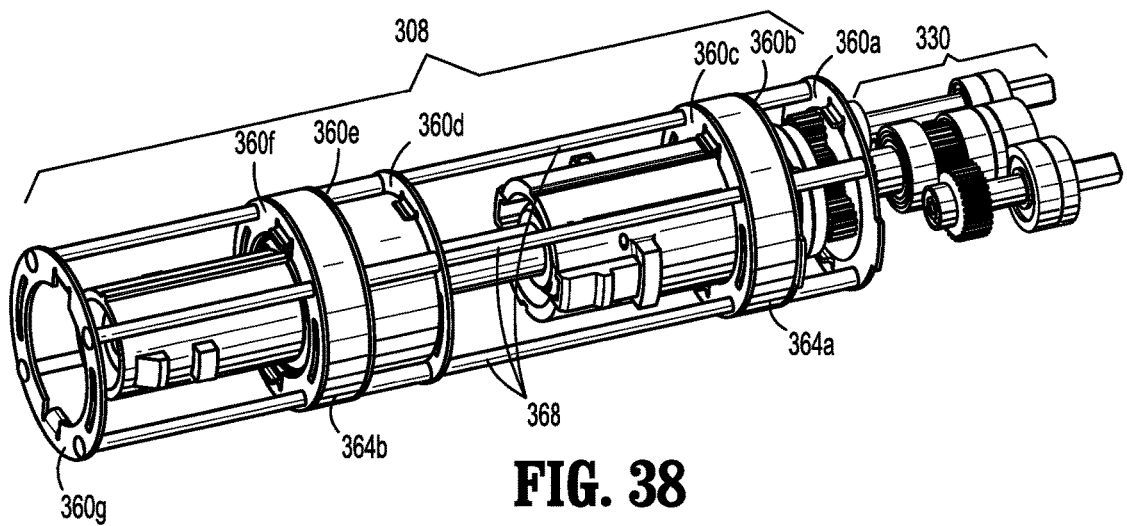
FIG. 38 is a perspective side view of adapter assembly of FIG. 37 with a base and housing members removed.
Figure 39:
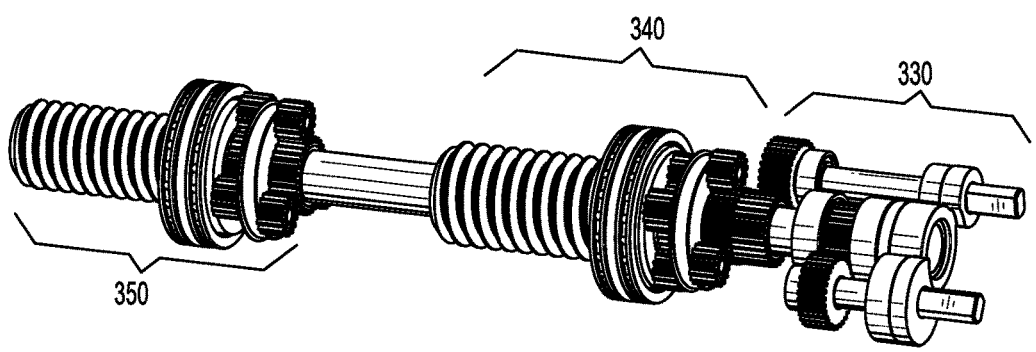
FIG. 39 is a perspective side view of the adapter assembly of FIG. 38 with a support structure removed.
Figures 40, 41:
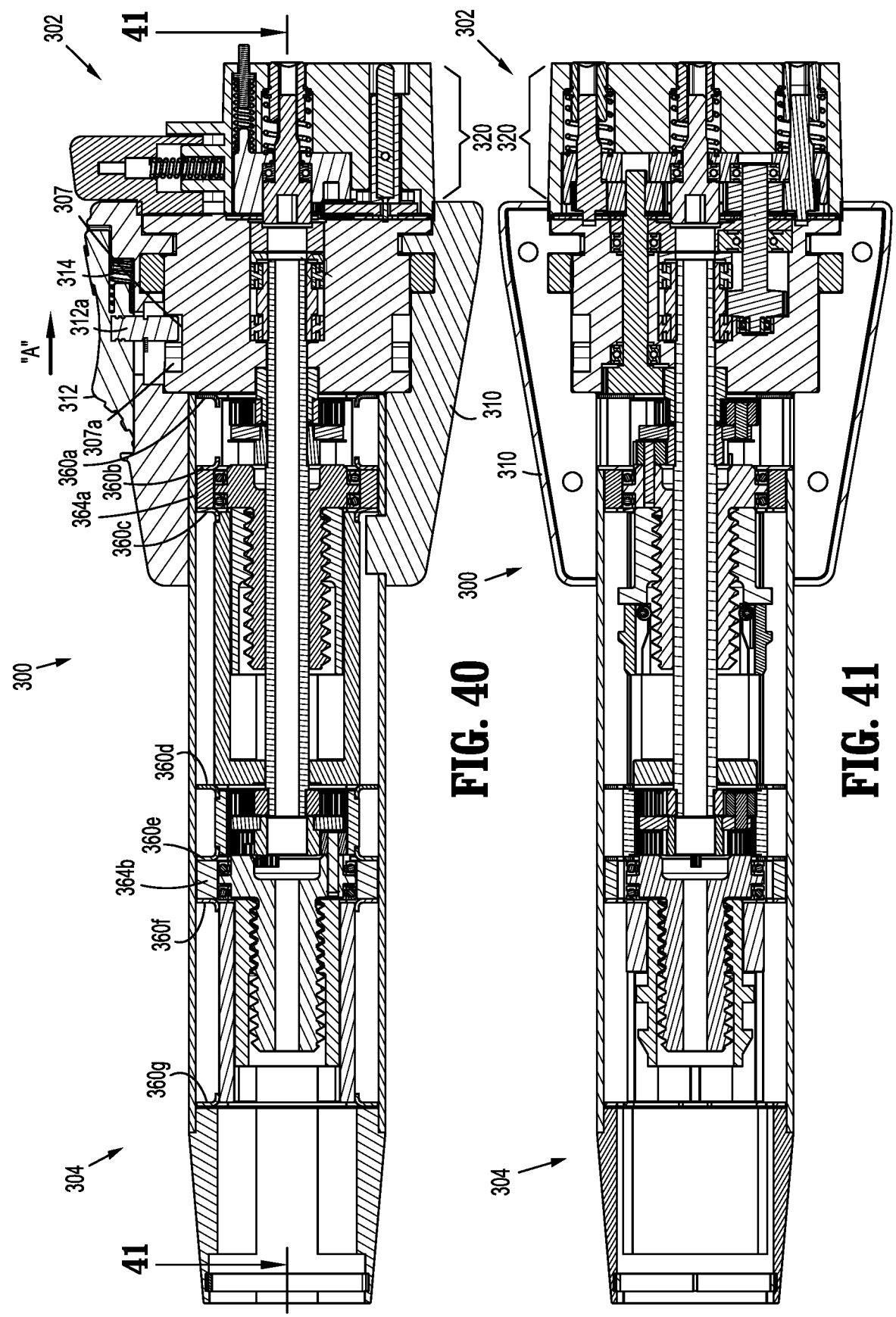
FIG. 40 is a cross-sectional side view taken along line 40-40 of FIG. 36.
FIG. 41 is a cross-sectional side view taken along line 41-41 of FIG. 40.

With reference now to FIGS. 34 and 35, extension assembly 200 is connected to adapter assembly 100 by receiving proximal end 202 (FIG. 17) of extension assembly 200 within distal end 104 of adapter assembly 100. In particular, first and second connection extensions 220, 240, 222, 242 of respective inner and outer flexible band assemblies 210, 230 are received within sleeve 106 of adapter assembly 100 such that tabs 178 of pusher member 170 of first pusher assembly 160 of adapter assembly 100 are received within openings 241, 243 of respective first and second connection extensions 240, 242 of outer flexible band assembly 230 to secure outer flexible band assembly 230 with first pusher assembly 160 and tabs 198 of pusher member 190 of second pusher assembly 180 of adapter assembly 100 are received within openings 221, 223 of first and second connection extensions 221, 223 of inner flexible band assembly 210 to secure inner flexible band assembly 210 with second pusher assembly 180.

As noted above, adapter assembly 100 may include a drive shaft 108 (FIG. 3) that extends from distal end 104 of adapter assembly 100. Prior to receipt of proximal portion 202 of extension assembly 200 within distal end 104 of extension assembly 100, drive shaft 108 is removed from adapter assembly 100. As proximal portion 202 of extension assembly 200 is received within distal end 102 of adapter assembly 100, proximal end 286a (FIG. 17) of second drive shaft 286 (FIG. 17) is received within socket 145 of drive member 140 of drive transfer assembly 130 of extension assembly 100 (FIG. 12).

After extension assembly 200 is operably engaged with adapter assembly 100, and adapter assembly 100 is operably engaged with surgical device 10 (FIG. 1), loading unit 40 (FIG. 34) of end effector 30 (FIG. 34) may be attached to connector assembly 290 of extension assembly 200 and an anvil assembly 50 (FIG. 34) may be attached to distal end 274b of trocar 274 of extension assembly 200 in a conventional manner. During actuation of loading unit 40 and anvil assembly 50, longitudinal advancement of pusher member 190 of second pusher assembly 180 of adapter assembly 100, as described above, and as indicated by arrows "C" in FIG. 35A, causes longitudinal advancement of outer flexible band assembly 230 of extension assembly 200 and longitudinal advancement of pusher member 170 of first pusher assembly 160, as described above, and as indicated by arrows "D" in FIG. 35A, causes longitudinal advancement of inner flexible band assembly 210. Rotation of drive shaft 108 in a first direction, as described above, and as indicated by arrow "E", causes advancement of trocar 274 of extension assembly 200. Conversely, longitudinal retraction of pusher member 190 causes longitudinal retraction of outer flexible band assembly 230, longitudinal retraction of pusher member 170 causes longitudinal retraction of inner flexible band assembly 210, and rotation of drive shaft 108 in a second direction causes retraction of trocar 274 of extension assembly 200.

In embodiments, inner flexible band assembly 210 operably connects second pusher assembly 180 of adapter assembly 100 with a knife assembly (not shown) of loading unit 40 (FIG. 34) of end effector 30 (FIG. 34) attached to connector assembly 290 of extension assembly 200. Outer flexible band assembly 230 operably connects first pusher assembly 160 of adapter assembly 100 with a staple driver assembly (not shown) of loading unit 40. Trocar assembly 270 operably connects drive transfer assembly 130 of adapter assembly 100 to anvil assembly 50 (FIG. 34) of end effector 30 (FIG. 34). In this manner, operation of second pusher assembly 160 causes longitudinal movement of inner flexible band assembly 210 which causes longitudinal movement of the knife assembly, operation of first pusher assembly 180 causes longitudinal movement of outer flexible band assembly 230 which causes longitudinal movement of the staple driver assembly, and operation of drive transfer assembly 130 causes longitudinal movement of trocar 274 which causes longitudinal movement of anvil assembly 50 relative to loading unit 40.

By stacking first and second pusher assemblies 160, 180 of adapter assembly 100, as described, and positioning the drive shaft 108 of the transfer assembly 130 through first and second pusher assemblies 160, 180, adapter assembly 100 can perform three functions through an access port or other opening (not shown) having a small diameter, e.g., 21 mm. Similarly, by configuring inner flexible band assembly 210 within outer flexible band assembly 230 and receiving trocar assembly 270 through the inner and outer flexible band assemblies 210, 230, extension assembly 200 can perform three functions through an access port or other opening (not shown) having a small diameter, e.g., 21 mm.

With reference to FIGS. 36-41, an adapter assembly according to another embodiment of the present disclosure is shown as adapter assembly 300. Adapter assembly 300 is substantially similar to adapter assembly 100 described hereinabove and will only be described as relates to the differences therebetween.

As will become apparent from the following description, the configuration of adapter assembly 300 permits rotation of a distal portion 304 of adapter assembly 300 about a longitudinal axis "x" (FIG. 36), relative to a proximal portion 302 of adapter assembly 300. In this manner, an end effector, e.g. end effector 30 (FIG. 34) secured to distal portion 304 of adapter assembly 300 or an end effector secured to an extension assembly, e.g., extension assembly 200 (FIG. 17) which is secured to distal portion 304 of adapter assembly 300 is rotatable about longitudinal axis "x" independent of movement of the surgical device (not shown) to which adapter assembly 300 is attached.

Adapter assembly 300 includes a base 306 and a support structure 308 rotatable relative to base 306 along longitudinal axis "x" of adapter assembly 300. A rotation handle 310 is rotatably secured to base 306 and fixedly secured to a proximal end of support structure 308. Rotation handle 310 permits longitudinal rotation of distal portion 304 of adapter assembly 300 relative to proximal end 302 of adapter assembly 300. As will be described in further detail below, a latch 312 is mounted to rotation handle 310 and selectively secures rotation handle 310 in a fixed longitudinal position.

Proximal portion 302 of adapter assembly 300 includes a drive coupling assembly 320 and a drive transfer assembly 330 operably connected to drive coupling assembly 320. Distal portion 304 of adapter assembly 300 includes a first pusher assembly 340 operably connected to drive transfer assembly 330, and a second pusher assembly 350 operably connected to drive transfer assembly 330. Drive coupling assembly 320 and drive transfer assembly 330 are mounted within base 306, and thus, remain rotationally fixed relative to the surgical device (not shown) to which adapter assembly 300 is attached. First pusher assembly 340 and second pusher assembly 350 are mounted within support structure 308, and thus, are rotatable relative to the surgical device (not shown) to which adapter assembly 300 is attached.

Drive coupling assembly 320 is configured to selectively secure adapter assembly 300 to a surgical device (not shown). For a detailed description of an exemplary surgical device and drive coupling assembly, please refer to commonly owned U.S. Provisional Patent Application Ser. No. 61/913,572, filed Dec. 9, 2013, the content of which is incorporated by reference herein in its entirety.

Rotation knob 310 is rotatably secured to base 306. Latch 312 includes a pin 312a (FIG. 38) configured to lock rotation knob 310 relative to base 306. In particular, pin 312a of latch 312 is received within a slot 307 formed in base 306 and is biased distally by a spring 314 into a notch 307a (FIG. 40) formed in base 306 and in communication with slot 307 to lock rotation knob 310 relative to base 306. Proximal movement of latch 312, as indicated by arrow "F" in FIG. 38, retracts pin 312a from within notch 307a to permit rotation of rotation knob 310 relative to base 306. In embodiments, base 306 defines a second notch (not shown) diametrically opposed to notch 307a for locking rotation knob 310 in a first longitudinal orientation when pin 312a of latch 312 is received within notch 307a and in a second longitudinal orientation that is one-hundred eighty degrees (180°) rotated from the first longitudinal orientation when the pin 312a of latch 312 is received within the second notch. Alternatively, it is envisioned that base 306 may define a number of notches radially spaced about base 306 and in communication with slot 307 that permit rotation knob 310 to be locked in a number of longitudinal orientations relative to base 306.

Drive transfer assembly 330, first drive pusher assembly 340, and second drive pusher assembly 350 of adapter assembly 300 are substantially identical to respective drive transfer assembly 130, first drive pusher assembly 160, and second drive pusher assembly 180 of adapter assembly 100 described hereinabove, and therefore, will only be described as relates to the differences therebetween.

Support structure 308 is fixedly received about first and second drive pusher assemblies 340, 350 and rotatably relative to base 306. As noted above, rotation knob 310 is fixedly secured to the proximal end of support structure 308 to facilitate rotation of support structure 308 relative to base 306. Support structure 308 is retained with outer sleeve 305 of adapter assembly 300 and is configured to maintain axial alignment of first and second drive pusher assemblies 340, 350. Support structure 308 may also reduce the cost of adapter assembly 300 when compared to the cost of adapter assembly 100.

Support structure 308 respectively includes first, second, third, fourth, fifth, sixth, and seventh plates 360a, 360b, 360c, 360d, 360e, 360f, 360g, first and second pluralities of tubular supports 362a, 362b, first and second support rings 364a, 364b, first and second plurality of ribs 366a, 366b, and a plurality of rivets 368. From proximal to distal, first and second plates 360a, 360b are maintained in spaced apart relation to each other by the first plurality of tubular supports 362a, second and third plates 360b, 360c are maintained in spaced apart relation to each other by first support ring 364a, third and fourth plates 360c, 360d are maintained in spaced apart relation to each other by first plurality of support ribs 366a, fourth and fifth plates 360d, 360e are maintained in spaced apart relation to each other by second plurality of tubular supports 362b, fifth and sixth plates 360e, 360f are maintained in spaced apart relation to each other by a second support ring 364b, and sixth and seventh plates 360f, 360g are maintained in spaced apart relation to each other by second plurality of support ribs 366b. First, second, third, fourth, fifth, sixth, and seventh plates 360a-g are held together by a plurality of rivets 368 secured to first and seventh plates 360a, 360g and extending through second, third, fourth, fifth, and sixth plates 360b-360f, first and second support rings 364a, 364b, and respective first and second plurality of tubular support 362a, 362b.

Adapter assembly 300 operates in a substantially similar manner to adapter assembly 100 described hereinabove. In addition, as described in detail above, adapter assembly 300 is configured to permit rotation of an end effector, e.g., end effector 30 (FIG. 34) attached to adapter assembly 300 or attached to an extension assembly that is attached to adapter assembly 300 to be selectively rotated about longitudinal axis "x" (FIG. 36) during use.

Figure 42:
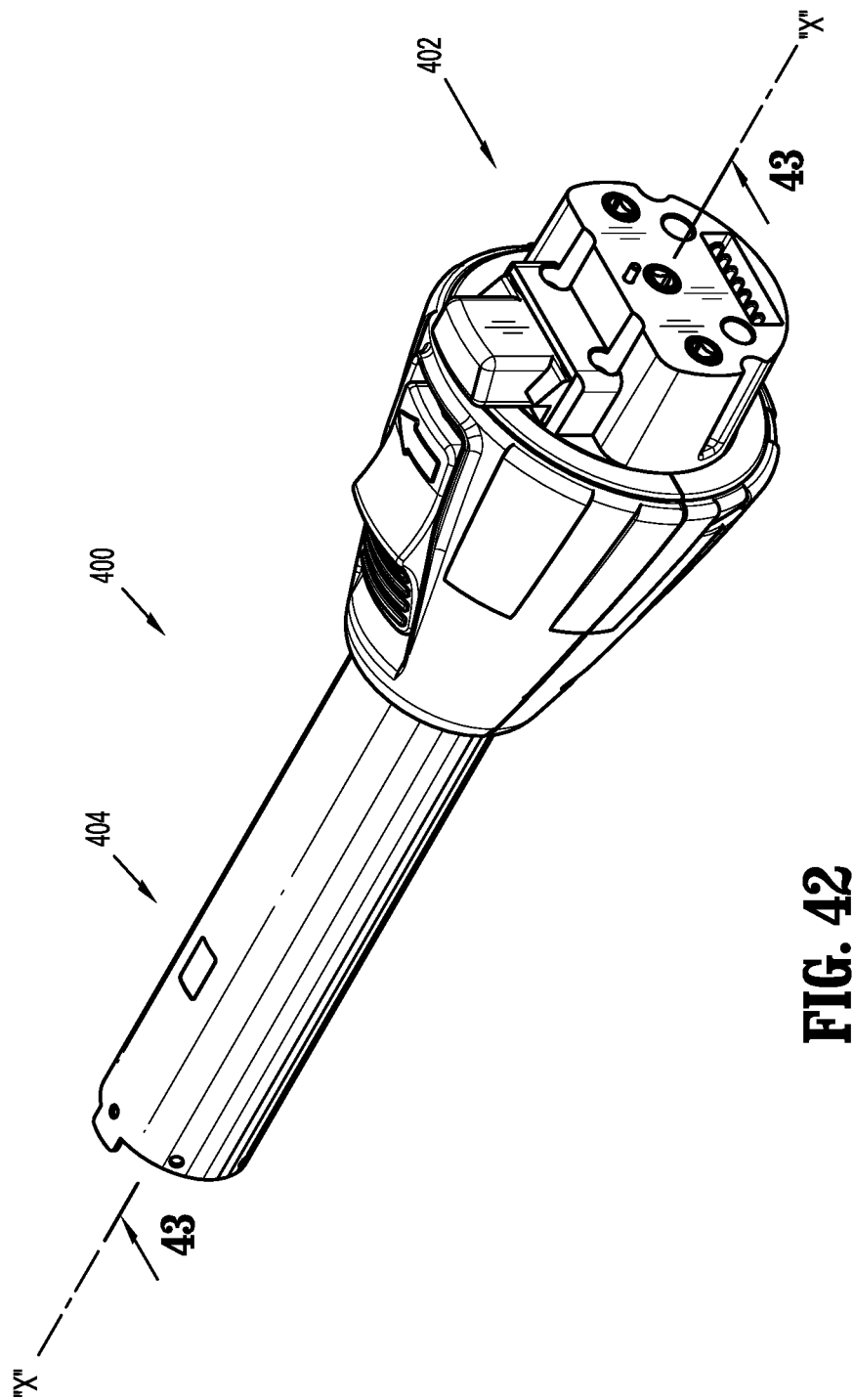
FIG. 42 is a rear, perspective view of an adapter assembly according to yet another embodiment of the present disclosure.
Figure 45:
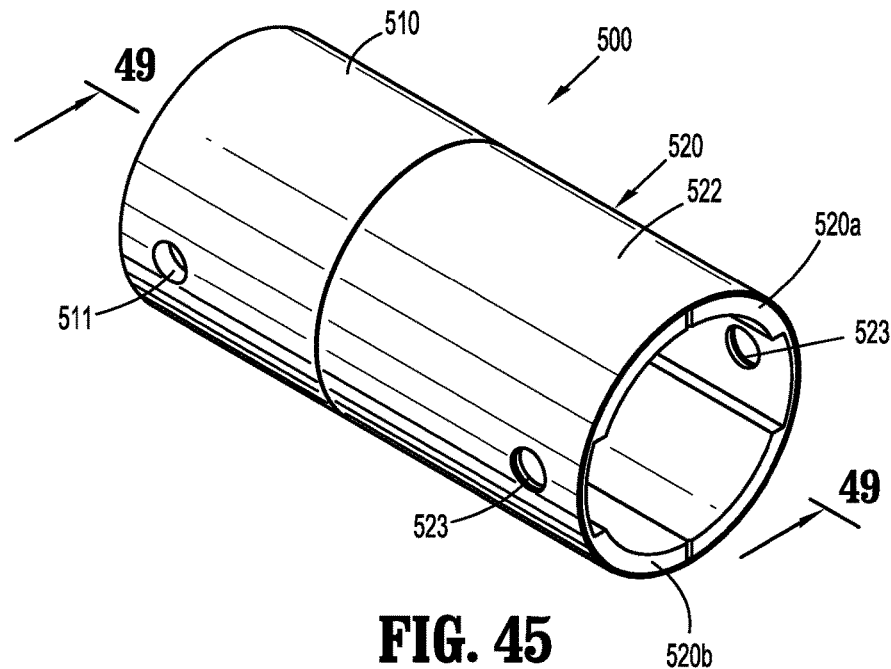
FIG. 45 is a perspective view of a connector assembly according to an embodiment of the present disclosure.
Figure 46:
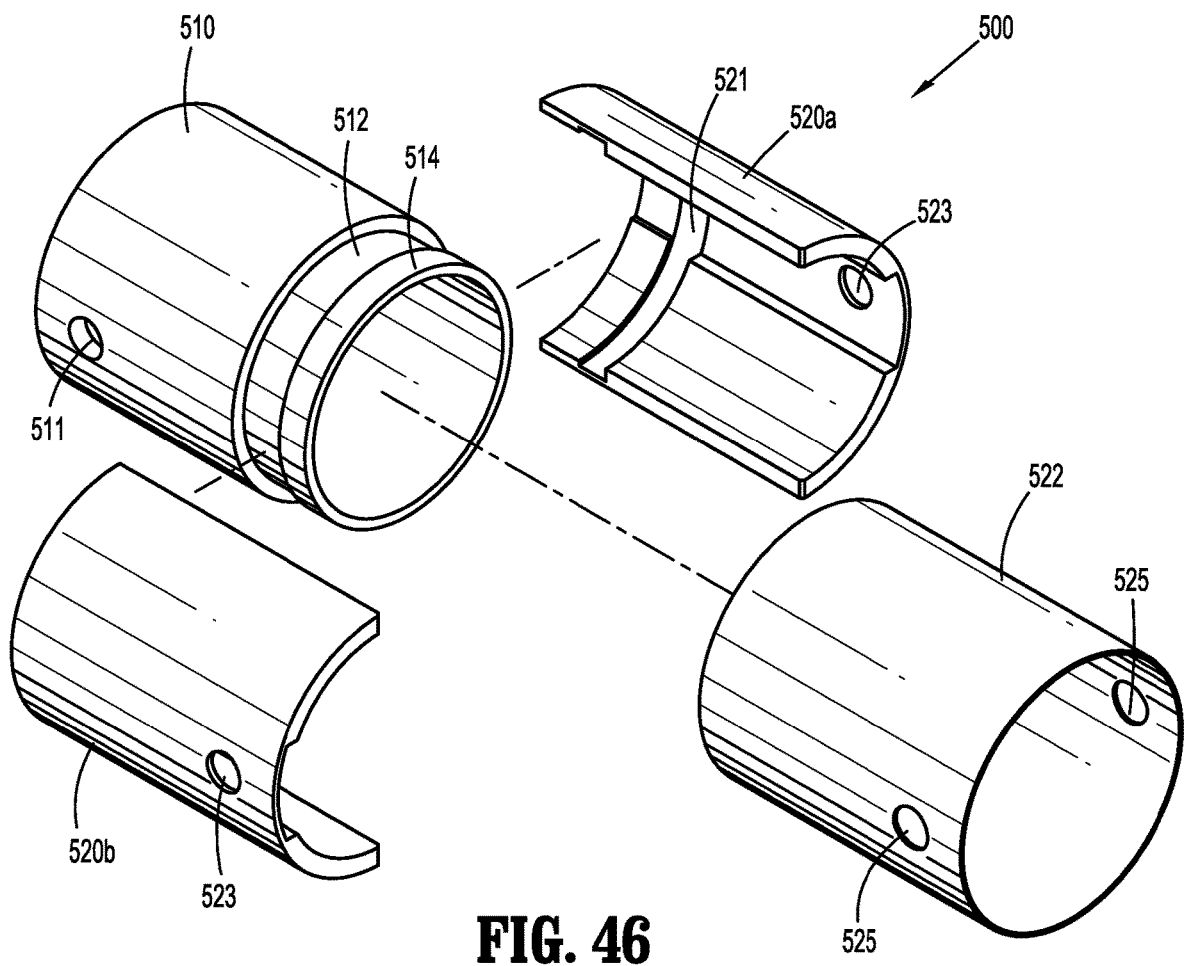
FIG. 46 is an exploded perspective view of the connector assembly of FIG. 45.
Figure 47:
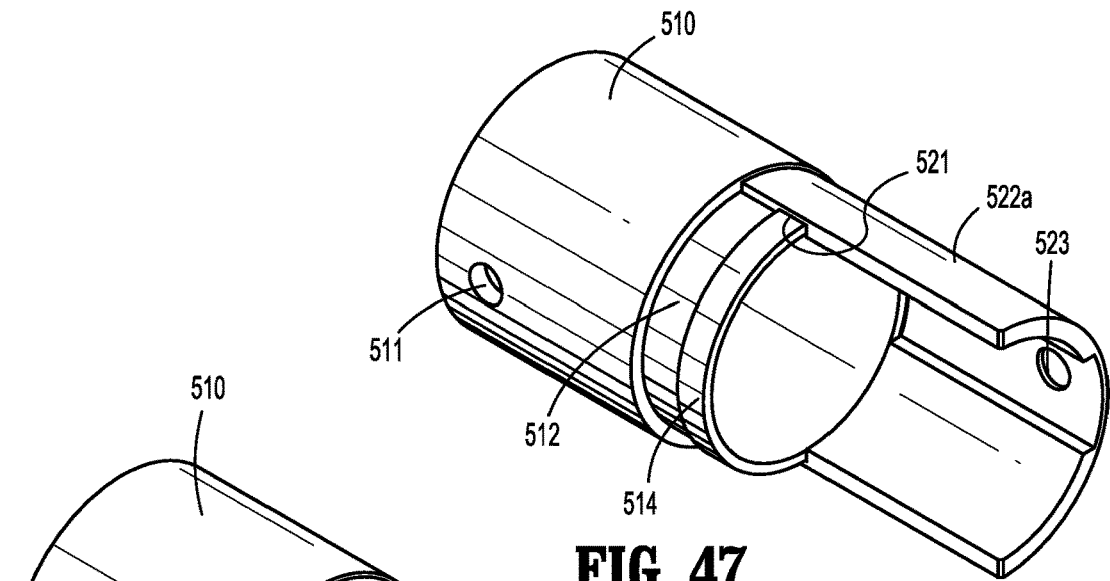
FIG. 47 is a perspective view of the connector assembly of FIG. 45 with a sleeve and first section of a tubular extension removed.
Figure 48:
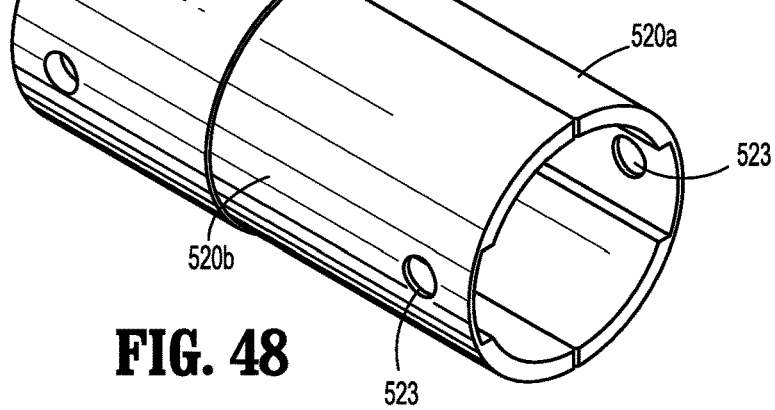
FIG. 48 is a perspective view of the connector assembly of FIG. 45 with the sleeve removed.
Figure 49:
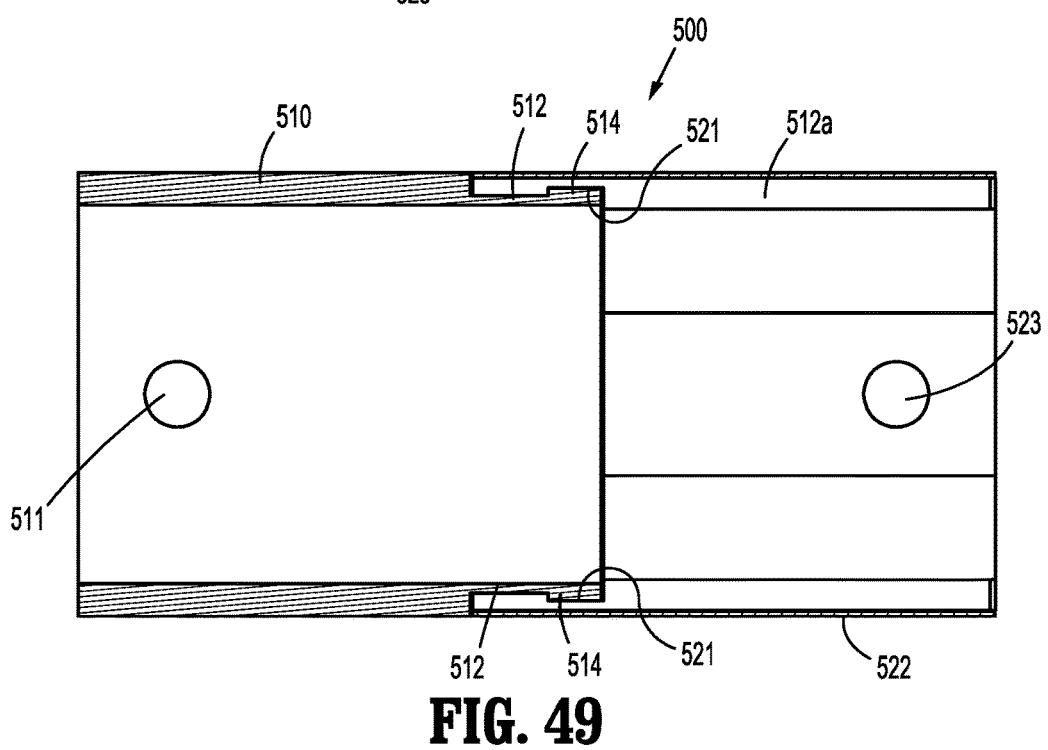
FIG. 49 is a cross-sectional side view taken along line 49-49 of FIG. 45.

With reference now to FIGS. 42-44, an adapter assembly according to another embodiment of the present disclosure is shown generally as adapter assembly 400. Adapter assembly 400 is substantially similar to adapter assemblies 100 and 300 described hereinabove, and therefore will only be described as relates to the differences therebetween.

Adapter assembly 400 includes a proximal portion 402 and a distal portion 404 rotatable along a longitudinal axis "x" relative to proximal portion 402. Distal portion 404 includes a support structure 408 secured to outer sleeve 405 and formed about first and second pusher assemblies 440, 450. Support structure 408 includes a plurality of reinforcing members 462 extending substantially the length of outer sleeve 405. Reinforcing members 462 each include a proximal tab 462a and a distal tab 462b which extend through outer sleeve 405 to secure reinforcing member 462 within outer sleeve 405. Proximal tabs 462 of reinforcing members 462 are further configured to engage a rotation knob 410 of adapter assembly 400. Adapter assembly 400 may include annular plates (not shown) positioned radially inward of reinforcing members 462 that maintain proximal and distal tabs 462a, 462b of reinforcing members 462 in engagement with outer sleeve 405. The annular plates may also provide structure support to distal portion 404 of adapter assembly 400. The configuration of adapter assembly 400 allows for a single tube, e.g. outer sleeve 405, for containing the drive components. With reference to FIGS. 45-49, a connection assembly according to an embodiment of the present disclosure is shown generally as connection assembly 500. As shown and will be described, connection assembly 500 is configured to be attached to first and second tubular bodies (not shown) for connecting the first tubular body, i.e., adapter assembly 100 (FIG. 3), 300 (FIG. 36), 400 (FIG. 42), to the second tubular body, i.e., extension assembly 200 (FIG. 17). It is envisioned, however, that the aspects of the present disclosure may be incorporated directly into the first and second tubular bodies to permit connection of the first tubular body directly to the second tubular body.

Connection assembly 500 includes a tubular base 510 and a tubular extension 520 formed of first and second sections 520a, 520b and an outer sleeve 522. As shown, tubular base 510 defines a pair of openings 511 for securing tubular base 510 to a first tubular body (not shown). Alternatively, tubular base 510 may include only a single opening, one or more tabs (not shown), and/or one or more slots (not shown), for securing tubular base 510 to the first tubular body (not shown). A flange 512 extends from a first end of tubular base 510 and includes an annular rim 514 extending thereabout.

First and second sections 520a, 520b of tubular extension 520 are substantially similar to one another and each define a groove 521 formed along an inner first surface thereof. Each of first and second section 520a, 520b of tubular extension 520 is configured to be received about flange 512 of tubular base 510 such that rim 514 of tubular base 510 is received within grooves 521 of first and second sections 520a, 520b of tubular extension 520. Once first and second sections 520a, 520b of tubular extension 520 are received about flange 512 of tubular base 510, outer sleeve 522 of tubular extension 520 is received about first and second sections 520a, 520b of tubular extension 520 to secure tubular extension 520 to tubular base 510.

As shown, each of first and second sections 520a, 520b of tubular extension 520 define an opening 523 configured to be aligned with a pair of openings 525 in outer sleeve 522 to secure outer sleeve 522 to first and second sections 520a, 520b. Either or both of first and second sections 520a, 520b and outer sleeve 522 may include one or more tabs, and/or one or more slots for securing outer sleeve 522 about first and second extensions. Alternatively, outer sleeve 522 may be secured to first and second sections 520a, 520b in any suitable manner.

Outer sleeve 522 may be selectively secured about first and second extensions for selective removal of outer sleeve 522 from about first and second sections 520a, 520b to permit separation of tubular extension 520 from tubular base 510. Alternatively, outer sleeve 522 may be permanently secured about first and second section to prevent tubular extension 520 from being separated from tubular base 510. As noted above, although tubular base 510 and tubular extension 520 are shown and described as forming an independent connection assembly 500, it is envisioned that tubular base 510 may be formed on a first tubular member, i.e., adapter assembly 100 (FIG. 3) and tubular extension 520 may be formed on a second tubular member, i.e., extension assembly 200 (FIG. 17) such that the first tubular member may be directly connected to the second tubular member.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An extension assembly for operably connecting an end effector to an electrosurgical instrument, the extension assembly comprising:
  an outer sleeve having a fixed curvature;
  a frame assembly received within the outer sleeve;
  an inner flexible band assembly slidably disposed within the frame assembly for performing a first function;
  an outer flexible band assembly disposed within the frame assembly and radially outward of the inner flexible band assembly, the outer flexible band assembly being moveable relative to the frame assembly and the inner flexible band assembly for performing a second function; and a trocar assembly disposed within the frame assembly radially inward of the inner flexible band assembly, and including a trocar member for performing a third function, wherein a proximal end of the trocar assembly is configured for connection to a rotatable drive shaft and rotation of the rotatable drive shaft cause linear advancement of the trocar member.

2. The extension assembly of claim 1, wherein the inner flexible band assembly includes a proximal end configured for connection to a first linear drive member and the outer flexible band assembly includes a proximal end configured for connection to a second linear drive member.

3. The extension assembly of claim 1, further including a connection assembly configured for operable connection with an end effector.

4. The extension assembly of claim 1, wherein a distal end of the inner flexible band assembly includes a flange configured for operable connection with an end effector.

5. The extension assembly of claim 1, wherein a distal end of the outer flexible band assembly includes a flange configured for operable connection with an end effector.

6. The extension assembly of claim 1, wherein the trocar member is configured for operable connection with an anvil assembly.

7. The extension assembly of claim 1, further including a link assembly for operable connection with the trocar assembly, the link assembly including a first shaft pivotally secured to a second shaft and a coupling member.

8. The extension assembly of claim 1, wherein the outer sleeve includes proximal and distal ends and the frame assembly includes at least one seal member, the at least one seal member creating a seal between the proximal and distal ends of the outer sleeve.

9. The extension assembly of claim 1, wherein the outer sleeve is curved along its length.

10. The extension assembly of claim 1, wherein the inner and outer flexible band assemblies each include first and second flexible bands.

11. An extension assembly for operably connecting an end effector to a surgical instrument, the extension assembly comprising:
    an outer sleeve having proximal and distal portions, the outer sleeve being rigid;
    a frame assembly received within the outer sleeve;
    an inner flexible band assembly slidably disposed within the frame assembly, for performing a first function;
    an outer flexible band assembly slidably disposed within the frame assembly and relative to the inner flexible band assembly, for performing a second function, the inner and outer flexible band assemblies each including first and second flexible bands, the inner flexible band assembly being disposed radially inward of the outer flexible band assembly; and
    a trocar assembly disposed within the frame assembly radially inward of the inner flexible band assembly, and including a trocar member for performing a third function.

12. The extension assembly of claim 11, wherein the inner flexible band assembly includes a proximal portion configured for connection to a first linear drive member and the outer flexible band assembly includes a proximal portion configured for connection to a second linear drive member.

13. The extension assembly of claim 11, further including a connection assembly configured for operable connection with an end effector.

14. The extension assembly of claim 11, wherein a distal portion of the inner flexible band assembly includes a flange configured for operable connection with an end effector.

15. The extension assembly of claim 11, wherein a distal portion of the outer flexible band assembly includes a flange configured for operable connection with an end effector.

16. The extension assembly of claim 11, wherein the frame assembly includes at least one seal member, the at least one seal member forming a seal between the proximal and distal portions of the outer sleeve.

17. The extension assembly of claim 11, wherein the outer sleeve is curved between the proximal and distal portions.

18. An extension assembly for operably connecting an end effector to an electrosurgical instrument, the extension assembly comprising:
    an outer sleeve;
    a frame assembly received within the outer sleeve;
    an inner flexible band assembly slidably disposed within the frame assembly for performing a cutting function;
    an outer flexible band assembly slidably disposed within the frame assembly and relative to the inner flexible band assembly for performing a stapling function, the outer flexible band assembly including a first flexible band and a spaced apart second flexible band and the inner flexible band assembly including a first flexible band and a spaced apart second flexible band, the inner flexible band assembly being disposed between the first and second flexible bands of the outer flexible band assembly; and
    a trocar assembly disposed within the frame assembly radially inward of the inner flexible band assembly, and including a trocar member for performing a clamping function.

* * * * *